(12) United States Patent
Corzani

(10) Patent No.: US 11,306,227 B2
(45) Date of Patent: Apr. 19, 2022

(54) HOT-MELT ADHESIVES COMPRISING A BIMODAL POLYMER COMPOSITION FORMED BY POLYOLEFINS HAVING LOW STEREOSPECIFICITY

(71) Applicant: SAVARE' I.C. S.P.A., Milan (IT)

(72) Inventor: Italo Corzani, Milan (IT)

(73) Assignee: SAVARE' I.C. S.P.A., Milan (IT)

( * ) Notice: Subject to any disclaimer, the term of this patent is extended or adjusted under 35 U.S.C. 154(b) by 0 days.

(21) Appl. No.: 17/057,314

(22) PCT Filed: May 20, 2019

(86) PCT No.: PCT/IB2019/054143
§ 371 (c)(1),
(2) Date: Nov. 20, 2020

(87) PCT Pub. No.: WO2019/229577
PCT Pub. Date: Dec. 5, 2019

(65) Prior Publication Data
US 2021/0189199 A1 Jun. 24, 2021

(30) Foreign Application Priority Data
May 28, 2018 (IT) ........................ 102018000005783

(51) Int. Cl.
*A61F 13/15* (2006.01)
*C09J 123/14* (2006.01)
*A61F 13/472* (2006.01)
*A61F 13/496* (2006.01)

(52) U.S. Cl.
CPC ........ *C09J 123/14* (2013.01); *A61F 13/15577* (2013.01); *A61F 13/15585* (2013.01); *A61F 13/472* (2013.01); *A61F 13/496* (2013.01); *A61F 2013/1591* (2013.01)

(58) Field of Classification Search
CPC .............. C09J 123/14; A61F 13/15577; A61F 13/15585; A61F 13/472; A61F 13/496; A61F 2013/1591
See application file for complete search history.

(56) References Cited

U.S. PATENT DOCUMENTS

| | | | |
|---|---|---|---|
| 4,120,916 A | 10/1978 | Meyer, Jr. et al. | |
| 5,912,295 A * | 6/1999 | Oeltjen | |
| 6,486,246 B1 | 11/2002 | Vion | |
| 6,747,114 B2 | 6/2004 | Karandinos et al. | |
| 6,872,279 B1 | 3/2005 | Kolowrot et al. | |
| 8,623,480 B2 | 1/2014 | Davis | |
| 8,865,824 B2 | 10/2014 | Bunnelle | |
| 9,670,388 B2 | 6/2017 | Bunnelle | |
| 9,695,341 B2 | 7/2017 | Thatcher et al. | |
| 9,695,342 B2 | 7/2017 | Sustic et al. | |
| 2007/0281118 A1* | 12/2007 | Miller | |
| 2013/0295380 A1* | 11/2013 | Merrill | |
| 2014/0324006 A1* | 10/2014 | Zhong | |
| 2015/0173958 A1 | 6/2015 | Bunnelle et al. | |
| 2015/0174281 A1 | 6/2015 | Bunnelle | |
| 2015/0174286 A1 | 6/2015 | Bunnelle | |
| 2018/0078425 A1 | 3/2018 | Bunnelle | |

FOREIGN PATENT DOCUMENTS

WO 2015095480 A1 6/2015

OTHER PUBLICATIONS

Evonik (Vestoplast ®828 Amorphous Polyalphaolefin, 1 page, accessed Apr. 13, 2021, accessed from http://www.matweb.com/search/datasheet.aspx?matguid=04e719c4cf2b4de9ae81bf235eb22470&ckck=1). (Year: 2021).*
Search Report and Written Opinion for International Application No. PCT/IB2019/054143 dated Aug. 12, 2019.
Search Report for Italian Application No. 102018000005783 dated Feb. 5, 2019.

* cited by examiner

*Primary Examiner* — Alma Pipic
(74) *Attorney, Agent, or Firm* — Pearne & Gordon LLP

(57) ABSTRACT

The present application discloses novel hot-melt adhesive formulations, with excellent processability, even in processes at high line-speed and at a relatively low temperature, the formulations suitable for strongly bonding substrates that have openings, holes, voids or pores, both macroscopic and microscopic ones, like perforated plastic films, both with bidimensional or tridimensional structure; fibrous substrates, both woven and non-woven; porous plastic films, and the like, all mentioned substrates being widely used for the manufacturing of absorbent hygienic articles. The hot-melt formulations include, as their main or even unique constituent, at least one polymer composition formed by two polyolefins, substantially non-stereospecific, as showed by the low value of their crystallization enthalpy at time zero, the polyolefins having average Number Molecular Weights Mn that do not differ for more than about 6,000 g/mole, being the single average Number Molecular Weights of said polyolefins ranging from about 3,000 g/mole and about 30,000 g/mole.

41 Claims, No Drawings

HOT-MELT ADHESIVES COMPRISING A BIMODAL POLYMER COMPOSITION FORMED BY POLYOLEFINS HAVING LOW STEREOSPECIFICITY

CROSS-REFERENCE TO RELATED APPLICATIONS

This is a National Stage application of PCT international application PCT/IB2019/054143, filed on May 20, 2019, which claims the priority of Italian Patent Application No. 102018000005783, filed May 28, 2018, both of which are incorporated herein by reference in their entirety.

FIELD OF THE INVENTION

The present invention discloses new hot-melt adhesive formulations, that show a novel and excellent processability, even in processes at high line-speed and at a relatively low temperature, said formulations being especially suitable for strongly bonding substrates that have openings, holes, voids or pores, both macroscopic and microscopic ones, like perforated plastic films, both with a bidimensional or a tridimensional structure; fibrous substrates, both woven and non-woven; porous plastic films, and the like, all said mentioned substrates being widely used in particular for the manufacturing of absorbent hygienic articles.

DEFINITIONS

The expressions "that comprise(s)" or "comprising" are used herein as open-ended terms, that specify the presence of what in the text follows said terms, but that does not preclude the presence of other ingredients or features, e.g. elements, steps, components, either known in the art or disclosed herein.

The expression "substantially free from" referred to a composition, formulation, chemical compound and its possible constituents or impurities, means that the constituent(s) from which it is said to be "substantially free" are not detectable in it by the most common techniques for chemical analyses.

The expression "at time zero" (e.g. referred to certain properties or to certain chemical or physical parameters of a polymer, or of a polymer composition or of an adhesive formulation that are "measured at time zero") means that said properties or parameters are measured or determined at a time, measured starting from the moment in which the material under test has solidified from the melt, that is sufficiently short so to avoid noticeable modifications in said properties or parameters, due to possible effects of "aging in time"/"variation in time". More specifically for all the polymers, polymer compositions and adhesive formulations discussed herein, "time zero" means a time that is not longer than two hours (120 minutes) after the solidification from the melt of the polymer, polymer composition or adhesive formulation under test.

Similarly the adjective "initial" or the adverb "initially", referred to certain properties or to certain chemical or physical parameters of a polymer, or of a polymer composition or of an adhesive formulation, has the same meaning of the above mentioned expression "at time zero". I.e. also the adjective "initial" or the adverb "initially", referred to certain properties or to certain chemical or physical parameters of a polymer, a polymer composition or an adhesive formulation means that those properties or those chemical or physical parameters are measured at a time not longer than 120 minutes from the solidification from the molten state of the material under test.

The expressions "aged" of "after aging" referred to certain properties or physical/chemical parameters mean that said properties or parameters are measured after an opportune period of time from their solidification from the melt. More specifically, some of the adhesive formulations disclosed herein have been surprisingly discovered to undergo a significant variation with time of some of their properties or of their main physical or chemical parameters (e.g. their rheological parameters and/or their crystallinity content). Generally the final stable asymptotic values for these parameters/properties that significantly change with time, are reached in times that can vary between one and ten days. For this scope, the materials under test are aged by conditioning them for seven days at 23° C. and 50% relative humidity after their solidification from the molten state.

For clarification purposes, when a certain property or a certain physical or chemical parameter of a polymer, of a polymer composition or of an adhesive formulation disclosed herein, is not accompanied by any attribute that specifies the moment in time at which it has been measured or determined (i.e. whether "at time zero"/in "initial" conditions or in "aged" conditions) it is implicitly meant that it has been measured/determined "at time zero"/in "initial" conditions, i.e. within no more than 120 minutes from the solidification from the melt of said material under test.

The expression, referred to two or more polymers "that have/having a substantially similar composition" means that said two or more polymers, in the case that they are homopolymers, are obviously formed by the same monomer. In the case that they are copolymers, o, more in general, polymers formed by two or more monomers, the expression means that:

they have the same main monomer, said "main monomer" meaning the monomer that is present in the larger molar fraction, or, as it happens in most cases, that is present for at least 50% by moles;

have the same secondary monomer or monomers, "secondary monomer(s)" meaning every monomer that is present at a level of least 25% by mole and the percentage by mole of each monomer (both main or secondary monomer(s)) present in the two or more polymers that are compared, does not differ for more than 10%.

The expression "copolymer(s)" means a polymer in whose chemical composition are present at least two monomers or more than two monomers. Therefore the term "copolymer(s)" herewith includes, unless it is specifically stated differently, not only polymers in whose chemical composition are present two different monomers, but also polymers in whose chemical composition are present three, four, five or more different monomers.

The equivalent expressions "Rheological Setting Point" or also "Temperature of Crossing of the Moduli" mean, in a rheological diagram in which are measured, as a function of Temperature, the rheological parameters Viscous Modulus G", Elastic Modulus G' and their ratio Tan Delta, the temperature at which the two Moduli cross (and at which therefore Tan Delta is equal to 1) in the field of temperatures above Room Temperature, i.e. above 23° C. Said rheological diagram, if it is measured in a "decreasing temperature mode" from hot to cold, with a sufficiently slow controlled cooling rate (e.g. 2° C./minute, as done in all the rheological experiments illustrated below) is very well simulating all the phenomena that occur between an adhesive and a substrate during the real processes of the application from the molten state of a hot-melt adhesive, and the consequent creation of an adhesive bond, during the slow natural spontaneous cooling and solidification/setting of the hot-melt.

In particular the "Rheological Setting Point" identifies that temperature at which the hot-melt adhesive, applied in the molten state on a certain substrate, starts to form the final adhesive bond in the solid state.

The expressions "that is (are) non-solid" are used herein to mean that a specific compound or material or ingredient or their blends, are in a physical state in which, even if they have a well definite volume, they do not have a fixed own shape, and they take the shape of the containers that contain them. Even in the case that they are sufficiently viscous to be temporarily shaped by themselves in any tridimensional shape, after being left at rest and without any external stress, apart from their own weight, they spontaneously flow and permanently deform, so to lose rather quickly (typically in a period of time that may vary between a few seconds and about one day) their initial shape, taking the shape of the containers that contain them (if these ones were not already full to the brim) or of the solid surface on which they are lying. Therefore this definition comprises all the materials that not only may be defined as "liquid" (both at high and low viscosity) according to the common meaning of this adjective, but also all those materials that, in the common language, are for example defined as "creamy", "pasty", "jelly-like", "gelatinous", "fluid", "greasy", "semi-solid" and the like. A further way of defining in rheological terms what, in the present invention, is meant when a certain compound or material or ingredient or their blends are said to be "non-solid" at room temperature, i.e. conventionally at the temperature of 23° C., is also by specifying that said "non-solid" matters can be defined as "rheologically liquid", i.e. as defined in Rheology, that they, at the specified temperature of 23° C., have a Viscous Modulus G" that is greater than their Elastic Modulus G', or also, what is equivalent by definition, that their Tan Delta is greater than 1.

"Room temperature", if not specifically defined in a different way, means a temperature equal to 23° C.; and "room conditions" means the conditions of an environment at a controlled temperature and relative humidity, at 23° C. and 50% relative humidity.

"Absorbent hygienic articles" refer to devices and/or methods concerning disposable absorbing and non-absorbing articles, that comprise diapers and undergarments for incontinent adults, baby diapers and bibs, training pants, infant and toddler care wipes, feminine catamenial pads, interlabial pads, panty liners, pessaries, sanitary napkins, tampons and tampon applicators, wound dressing products, absorbent care mats, detergent wipes, and the like.

"Perforated films" refers to films, typically made of plastic materials, like polyethylene, that are perforated with multiple holes, and that can have both a bidimensional or a tridimensional structure, and with a typical hole size in the range between a few hundred microns to about one millimeter, that are often used as components in absorbent hygienic articles.

"Fibrous substrates" refers to products having an essentially planar structure, formed by natural or synthetic fibers or their blends, both in the form of woven and of nonwoven fabrics, equally used as components in absorbent hygienic articles.

"Open Time" of an adhesive refers, especially for a hot-melt adhesive, to the interval of time during which, after its application from the melt on a first substrate, the adhesive is able to form sufficiently strong adhesive bonds for the intended use, with a second substrate that is brought into contact under moderate pressure with the first one. The open time of a holt-melt adhesive is herein measured according to the test method ASTM D 4497-94.

"Ring & Ball Softening Temperature" or "Point" refers to the softening temperature of a material, measured according to the test method ASTM D 36-95, in which all the test are completed within 120 minutes from the solidification from the melt of the material under test. Therefore all the Ring & Ball Softening Temperature Points reported herein are to be considered as measured at time zero/in initial conditions.

PRIOR ART

As it is well known to every averagely skilled person in the science of Adhesives and Adhesion, and as more in details explained in several basic books on this Science— among which e.g. are herein cited and incorporated by reference "Handbook of Adhesive Technology" by A. Pizzi and K. L. Mittal; "Handbook of Adhesives and Sealants" by E. M. Petrie and "Adhesion Science: Principle and Practice" by S. Abbott-the basic constituents of every non-reactive adhesive, and particularly of every hot-melt adhesive, are polymers, i.e. one polymer or a blend of two or more polymers.

In order to be sufficiently tacky and for sufficiently "wetting" the substrates to be bonded (in the peculiar sense by which the verb "to wet" is defined and used in the Science of Adhesion), it is necessary that, when the adhesive bond is formed, the adhesive is sufficiently "soft", i.e., in particular that, at the temperature of application and in the initial conditions of bond-formation, the adhesive has a sufficiently low value for its rheological parameter Elastic Modulus G'. Moreover, in order to increase as much as possible the "wetted" contact area between the adhesive and the substrate, so to maximize the adhesive strength that is proportional to said contact area, it is also required that the other rheological parameter Tan Delta, that expresses the ability of the adhesive to "flow" and contact/cover increasing areas of the substrate, is sufficiently high, again in the moment and conditions in which the adhesive bond is initially created.

Even if, through the addition of suitable low molecular weight additives, like e.g. through the addition of plasticizers and/or tackifiers, the basic polymer or polymers of an adhesive may be made softer and tackier than the pure polymer(s) in its/their original state, such formulation techniques have a practical limit in the maximum quantity of said low molecular weight additives that can be actually used. In fact if in the adhesive the percent concentration of polymer(s) becomes too small, the adhesive itself quickly loses cohesion, shows mechanical properties that are unacceptably poor, and even its adhesive strength becomes too low, because an adhesive bond, formed by an adhesive that is too low in cohesion and that is too mechanically weak, fails owing to the cohesive breaking of the adhesive itself.

It is therefore necessary that the polymer or blend of polymers themselves, that form the fundamental constituent(s) of an adhesive (independently from possible further minor modifications through formulation) are per se also sufficiently cohesive. Said in other terms, as it is well known to every averagely skilled person in the science of Adhesives and Adhesion, this means that polymers to be used in adhesives are typically polymers with a quite low crystallinity (a high crystallinity would make them too hard for this scope) and that have a Glass Transition Temperature (Tg), preferably not higher than room temperature, or better below room temperature, and in any case lower than the temperature at which said adhesives must adhere/are intended to be used.

For example, the first type of polymers that historically have been used as bases for excellent adhesive formulations, are elastomers, both natural, like natural rubber, and synthetic ones, that are amorphous polymers with very low Glass Transition Temperatures (Tg). For example natural rubber has a Tg of about −70° C.

It is therefore well known in the art that a polymer, for being a useful base for excellent adhesive formulations, besides having a sufficiently low Tg, for example at least below room temperature (as e.g. it happens for classes of polymers like Polyolefins), must also be selected so to have a low crystallinity and opportune rheological parameters (in particular a relatively low G' and a relatively high Tan Delta).

It is also obvious that, given the way in which hot-melt adhesives (to which the present invention and its discussion is specifically limited) form their adhesive bond with the substrate(s) on which they are applied in the molten state, i.e. during their spontaneous natural solidification from the melt and cooling, for example the level of crystallinity that plays a fundamental role in determining the initial adhesiveness/adhesive strength of the adhesive formulations disclosed herein, is primarily their crystallinity at time zero, i.e. their level of crystallinity spontaneously formed within 120 minutes from their solidification from the melt. Similar concepts may be repeated with reference to the rheological parameters.

However these different requirements may easily conflict among themselves, especially if, like in the present invention, one considers hot-melt adhesives that are processed and applied in the molten state, and that must have, at the high temperature of application, sufficiently low viscosities to be easily extruded and processed. Moreover if, as it is a scope also of the present invention, one wants to obtain hot-melt adhesives that can be applied in particular also on thermo-sensitive substrates, like e.g. plastic films having low melting point/low thermal deformation point, and/or on substrates that are unusually thin, like e.g. plastic films or non-wovens at low basis-weight (e.g. equal or lower than about 15 g/ml), it is necessary that said hot-melt adhesives have relatively low processing temperatures, typically in the range between about 150° C. and about 180° C., and in any case not higher than about 185° C., while it is simultaneously required that the same adhesives, in their solid state, have a sufficient cohesion and excellent mechanical properties.

As already mentioned, all these requirements for a hot-melt adhesive, may conflict among themselves. For example a robust crystalline structure in the polymer assures a good cohesion in the adhesive formulation and strong mechanical properties; but, as already seen, this is in contrast with the equally essential good initial adhesive properties. Vice versa, a polymer with too low initial crystallinity or practically fully amorphous (like for example an elastomer or an atactic polyolefin) might have an excellent initial adhesiveness, but very poor initial cohesion. This unacceptably low initial cohesion might be improved to acceptable levels by increasing the polymer's molecular weight to very high values, in the order of at least several hundreds of thousands g/mole. But obviously these too high molecular weights would prevent the use of such polymers as bases for hot-melt adhesives, because their molten viscosity would be extremely high even at very high temperatures, which facts would make impossible their processing in the molten state, and so on.

Therefore in the field of hot-melt adhesives there is a continuous need of obtaining an optimum equilibrium between different and contrasting requirements, like a low viscosity in the molten state, even at not too high temperatures, and a good cohesion/good mechanical properties in the solid state, all these requirements being combined also with sufficiently high tackiness of the adhesive, as a consequence of its high "softness" and good "wetting ability", i.e. of its relatively low crystallinity/low G'/high Tan Delta at the moment of its solidification from the melt.

The Prior Art has tried to satisfy these contrasting requirements by proposing different formulating criteria, in particular for hot-melt adhesives that are based on Polyolefins, both homopolymers and copolymers.

As base-polymers for hot-melt adhesives, Polyolefins show various advantages especially in comparison with many elastomers. For example polyolefins are polymers that are exceptionally stable to heat, and are therefore particularly suited to be processed in the molten state without any significant degradation; they are non-toxic, do not cause allergies, are chemically inert, colorless and odorless, and therefore they are particularly valued as baseconstituents in hot-melt adhesives for absorbent hygienic articles; they are also largely available on the market at generally rather low prices and so on.

This explains the commercial success obtained by hot-melt adhesives based on polyolefins.

For all the reasons already mentioned above, polyolefinic homopolymers and/or copolymers that can be used as main polymers in hot-melt adhesives, cannot be polyolefins that have a high crystalline level, like e.g. pure isotactic polypropylene (i-PP) or high-density polyethylene (HDPE). These polymers have a very high cohesion and excellent mechanical properties, but, even in case they would be formulated in opportune ways with various low molecular weight additives, like plasticizers and tackifiers, they would never be able to be made sufficiently soft and tacky to form strong adhesive bonds.

Therefore, some Prior Art has often utilized, in some hot-melt adhesives based on polyolefins, amorphous polyolefins, or anyhow polyolefins with a relatively low crystalline level, like e.g. atactic polypropylene or the so-called APAO copolymers (Atactic Poly-Alpha Olefins).

However, because the molecular weights of said polymers with low crystallinity, cannot be too high in order to avoid excessive viscosities in the molten state, the need of having anyhow a good cohesion and good mechanical properties in the final adhesive, has obliged most of the Prior Art to introduce into adhesive formulations based on polyolefins with low crystallinity, also a certain amount of other polymers, that are much more crystalline. In this way it is somehow possible to improve a bit the poor mechanical/cohesive properties of APAO's, but at the expense of the optimization of the adhesive properties of the adhesive formulation itself, because it is made less tacky because of the higher initial crystallinity.

For example, U.S. Pat. No. 6,747,114 describes hot-melt adhesives that are based on a semi-crystalline polypropylene. This type of polymer is requested to have a significant level of crystallinity (and therefore of "hardness"), as demonstrated by its high melting Enthalpy, generally comprised between about 30 J/g and about 80 J/g, but more preferably not lower than as much as 50 J/g.

The U.S. Pat. No. 6,486,246 describes hot-melt adhesives based on a blend of polyolefins. A fraction of said blend is said to be a fully amorphous copolymer of ethylene and propylene, its complete amorphous character being demonstrated by its asserted total solubility in xylene at 25° C. This fully amorphous polyolefin is certainly useful for obtaining a final adhesive formulation that is sufficiently soft, adhesive and tacky for the desired scope. However, the cohesion in the solid state of this formulation, in case it would be constituted exclusively by this amorphous polymer, would be so low that inventors are obliged to blend (and in substantial quantities) said basic amorphous polyolefin with as many as three other different polyolefinic polymers, all of them having a high crystallinity, as explicitly said or implicitly confirmed, by the fact that e.g. at least one of these additional polymers is expressly said to be completely insoluble in xylene at 25° C.

To emphasize how large can be the quantity of crystalline polymers that it is necessary to add to a base of amorphous polyolefin(s) in this Prior Art, we can e.g. refer to Examples 1 to 4 of the above mentioned patent. On a base of just 14.7 parts of fully amorphous polyolefin (60% by weight of 24.5 parts), inventors add 24.5 parts of a crystalline polypropylene homopolymer; plus 8.575 parts of a crystalline copolymer of propylene and ethylene; plus 1.225 parts of a copolymer of ethylene and propylene that has a particularly high crystallinity, as demonstrated by the fact that it is said to be completely insoluble in xylene at 25° C.

Therefore, on 49 total parts of polymeric base of the hot-melt adhesives illustrated in Examples 1 to 4 of U.S. Pat. No. 6,486,246, only 14.7 parts—i.e. only 30% by weight—is formed by a soft and tacky amorphous polyolefin, that is useful in forming good adhesive bonds; while as much as 70% of the formulation is a blend of various polymers, all of them with a high level of crystallinity and hardness, that are certainly useful in improving the initial cohesion of the adhesive, but that are also certainly detrimental for obtaining also a strong initial adhesiveness.

All this is even more confirmed by the fact that inventors, in order to get a level of adhesiveness that is somehow not too poor, are forced to add to the 49 parts of total polymeric fraction, as many as 52 parts of components at low molecular weight that may somehow favor an increase in initial adhesiveness, i.e. 30 parts of a Rosin tackifier and 22 parts of a plasticizing mineral oil.

This very high content of said additives at low molecular weight, may cause possible severe problems of various kind (as it will be explained more in details later); for example a powerful unpleasant odor, both during the use and even more during the application at high temperature in the molten state, that is typical of tackifiers, especially of Rosin-type tackifiers; possible toxic, sensitizing and/or allergenic effects; possible de-mixing and migration out of the formulation of the tackifiers and plasticizing oils at low molecular weight, with a consequent variation and degradation during time of the properties of the adhesive, and so on.

U.S. Pat. No. 4,120,916 describes polyolefin adhesive formulations that interestingly do not contain -besides various polyolefinic polymers, both amorphous and highly crystalline—any compounds at low molecular weight, like traditional plasticizers or tackifiers, that may generate bad odors, allergies or toxic effects, or that may create instabilities in the adhesive formulations. This is certainly an intriguing achievement, even if this formulation strategy causes, in the formulations disclosed by U.S. Pat. No. 4,120,916, a melt-viscosity that is excessively high, over what it is generally considered acceptable in most industrial applications for a good processability of a hot-melt adhesive.

In fact the adhesives that are disclosed there, are said to be applied at a temperature of 190° C., that is too high and unacceptable in most part of industrial uses of hot-melt adhesives, especially when the substrates to be bonded are thermo-sensitive substrates, like e.g. plastic films having low melting point/low thermal deformation point, and/or substrates that are unusually thin, like e.g. plastic films or non-wovens at low basis-weight, like the ones used in the manufacturing of absorbent hygienic articles.

In any case, the base polymer disclosed by U.S. Pat. No. 4,120,916 is an atactic polypropylene. Referring e.g. to the formulation disclosed in the Example of said patent, according to the inventors it is necessary—in order to have good cohesion characteristics in the adhesive—to add, to the 80% by weight of the highly adhesive atactic polypropylene, as much as 20% by weight of a 1:1 blend of two highly crystalline polyolefins, of which one is a crystalline polypropylene and one is a crystalline polyethylene. This high level of added crystallinity not only certainly negatively affects the tackiness and initial adhesiveness of the final formulation, but it also causes other negative effects for a hot-melt adhesive; for example, it increases the melting temperature (the added polypropylene is said to melt as high as 155° C.) and especially it makes excessively short the so-called "open time of the adhesive", a parameter that is expressly said to be equal just to 1 second.

As it is clear to every averagely skilled person in the art and in the processing/application of hot-melt adhesives, such a short open time, i.e. the fact that typically it cannot pass more than about 1 second between the application of the molten adhesive on a first substrate, and the contact with a second substrate to be bonded, if one wants to get a sufficiently strong adhesive strength, is a big limitation of the usefulness of this invention. In fact this influences and strongly limits the possibility that said hot-melt adhesives may be utilized also in slower processes and applications, in which a time-frame as short as 1 second, between the application of the molten adhesive and the bonding with the second substrate, may be an operative situation that is very difficult or, in some cases, even impossible to be achieved.

Also U.S. Pat. No. 9,695,342 discloses hot-melt adhesive formulations based on polyolefinic copolymers of propylene—ethylene and/or of propylene—butene, that have a rather low cristallinity and that, in order to show acceptably strong mechanical/cohesive properties, are blended—according to the disclosed Examples—with at least 10% to 15% by weight of a highly crystalline polymer, i.e. isotactic polypropylene with a high melting temperature (e.g. 157° C. for the preferred Polybond 3200) and whose viscosity in the molten state is anyhow excessively high, more preferably comprised between about 50,000 and 100,000 mPa·s.

As a consequence, in the disclosed Examples, are shown viscosities of the adhesive formulations between about 2,300 mPa·s and as much as 13,000 mPa·s, at the excessively high temperature of 190° C., which fact makes these hot-melt adhesive not usable in several industrial applications, especially in the manufacturing of absorbent hygienic articles.

Even according to U.S. Pat. No. 8,623,480, in formulations that are based on an amorphous polyolefin polymer, in order to have an acceptable equilibrium between a sufficiently good initial adhesiveness and a sufficient initial cohesion, it is indispensable to introduce crystalline or semi-crystalline polymers at high molecular weight, like e.g. the polyolefin elastomer known with the trade-mark Vistamaxx 6202. It is a polypropylene-polyethylene elastomer, that has crystalline segments formed by isotactic polypropylene, a high molecular weight and therefore a very high viscosity in the molten state, equal to about 700,000 mPa·s at 190° C. However, not even the addition of a polymer having such characteristics, seems to be apparently sufficient for reaching an acceptable cohesion. In fact the disclosed formulations contains, besides Vistamaxx, also rather high quantities, between 12% and 22% by weight, of waxes at high crystalline level, like in particular the polyethylenic wax Epolene N-21.

Such combination between additives at high molecular weight and waxes at high crystalline level, makes the hot-melt adhesive formulations disclosed in U.S. Pat. No. 8,623,480 to have solidification/setting times that are very short, in the order of 5.5 to 6 seconds. Even more, in the test-method for adhesive strength defined by U.S. Pat. No. 8,623,480, it is specified that, after the application of the molten adhesion on a first substrate, at the upmost one must let elapse no more than about 2 seconds before the first substrate is contacted under pressure with the second substrate, in order to form adhesive bonds that are sufficiently strong.

Such very short times between the application of the molten adhesive and the formation of the final bond, are, once again, a severe limitation for the usefulness of this invention, because this strongly limits the possibility for said hot-melt adhesives of being utilized also in slower processes and applications, in which a time as short as 2 seconds, between the application of the adhesive and the bonding of the other substrate, can be an operative situation very difficult or even sometimes impossible to be achieved.

U.S. Pat. No. 9,695,341 emphasizes, among the disclosed comparative Examples, the negative effects on a right balance between adhesive and cohesive properties of those formulations, that, in a hot-melt adhesive based on a substantially amorphous copolymer of polypropylene or polybutene, has the introduction of crystalline or semi-crystalline polymers, in particular if these polymers are at high molecular weight and at very high viscosity, like just the already mentioned elastomer Vistamaxx 6202 and other similar polymers.

Such negative effects appear even stronger, if we consider that most Prior Art teaches to formulate said adhesives, containing high molecular weight polymers, by introducing also large quantities of low molecular weight additives, as tackifiers and plasticizers. These low molecular weight additives are for sure effective in improving the tackiness and adhesiveness of the formulations; but, as already mentioned and as it is well known to every averagely skilled person in the science of hot-melt Adhesives, they lower the cohesion of the formulations, besides introducing further serious problems like a possible de-mixing during time from the core of the adhesive, a slow migration of the low molecular weight compounds out of the adhesive itself, unpleasant odors, possible toxic and sensitization effects and so on.

A possible solution to the intrinsic contradiction of these problems is advanced by U.S. Pat. No. 9,695,341 by proposing to formulate an adhesive containing, as its main polymer, an amorphous polyolefin, combined with substantial quantities (e.g. about 20% by weight each, in the Example 1, disclosed there) both of a tackifying resin, and, even more important, of a metallocenic crystalline propylene polymer. Said crystalline polymer proposed by U.S. Pat. No. 9,695,341 is chosen so to have both a molecular weight and a viscosity that are lower, for example, than the ones of the Vistamaxx cited in other Prior Arts; but these formulations of U.S. Pat. No. 9,695,341 are still affected by some drawbacks linked to the use of co-formulating ingredients that are crystalline polymers and that have anyhow a not sufficiently low viscosity.

For example, the metallocenic polypropylene L-Modu 400S, sold by Idemitsu Kosan (Japan), that is mentioned in said patent, is a polymer having a viscosity of 8,500 mPa·s at 190° C. and that contains in its polymeric chain, segments of isotactic polypropylene, i.e. segments that per se have a very high crystalline character and hardness. In fact the anyhow remarkable crystallinity of L-Modu 400S is highlighted by the fact that a Differential Scanning calorimetry (DSC) test, made in a heating mode on this pure polymer shows a melting Enthalpy of the crystalline part of as much as 28.92 J/g.

In U.S. Pat. No. 8,865,824 and 9,670,388, the same inventor discloses hot-melt adhesive formulations that are "substantially free" from tackifiers and that are based on a blend of two polymers plus a liquid plasticizer at low molecular weight, that is said to be preferably a poly-isobutylene oil (PIB), that is added in significant quantities (for example, up to about 25% by weight in the disclosed Examples), evidently in order to lower the viscosity of the final adhesives, that might be excessively high. The two polymers that are the bases of the hot-melt adhesive formulations disclosed in U.S. Pat. Nos. 8,865,824 and 9,670,388, are described as being a first "amorphous polymer" and a second crystalline "heterophase polymer". As examples of said "heterophase polymer" are specifically mentioned once again the polyolefin heterophase elastomers traded by ExxonMobil with the trade-mark Vistamaxx. In particular, in the Examples disclosed in U.S. Pat. Nos. 8,865,824 and 9,670, 388, it is used, as the second crystalline "heterophase polymer", Vistamaxx 8816, a polymer that presently is no more produced by Exxon and is no more available in the market. In this particular case, this specific grade of Vistamaxx is said to have a viscosity in the molten state that is lower than the one of other grades of Vistamaxx, like the Vistamaxx 6202 used by a different already mentioned Prior Art, and that is in any case lower than 20,000 mPa·s at 190° C.

However, what U.S. Pat. Nos. 8,865,824 and 9,670,388 lose in the cohesion of the final adhesive formulations, by decreasing the viscosity of the heterophasic and crystalline polyolefinic elastomer, must be somehow recovered by requiring that such second heterophasic polymer has a particularly high crystallinity.

Although the above mentioned two patents do not give any data about the crystallinity especially of the preferred Vistamaxx 8816, and although this datum cannot be any more experimentally measured, because the supplier has discontinued the production and sale of this Vistamaxx grade, however U.S. Pat. Nos. 8,865,824 and 9,670,388 certainly require that the second heterophasic polymer, that is mixed with the first amorphous polymer, has in general a very high crystallinity, more preferably between 25% and 70%, has shown by its melting enthalpy that is said to be possibly as high as 70 J/g. And although, as said above, a specific crystalline melting enthalpy value for Vistamaxx 8816 is not reported, however it is reasonable to deduce that said value is in any case very high, as e.g. specified for other two analogous crystalline heterophasic polyolefinic elastomers, mentioned there as equally suitable for that invention, i.e. Affinity GA 1950 and Affinity GA 1900, both supplied by Dow Chemical, that have respectively a melting enthalpy of as much as 53.4 J/g and 46.1 J/g.

It is therefore evident that in the Prior Art are not disclosed hot-melt adhesive formulations, based on polyolefinic homopolymers and/or copolymers, that show, at an optimum level, a balanced equilibrium of various very desirable characteristics, and of adhesive and processing properties correlated to such characteristics. In particular:

a high cohesion even in the presence of a very low level of initial crystallinity, said characteristic of a very low initial crystallinity that makes the adhesive, during its application from the melt and the adhesive bond formation, softer, tackier and with an "open time" sufficiently long so that it's suitable to be used in a wide range of different application processes and different line speeds;

an optimum adhesiveness on most types of substrates, but especially (as it will be better illustrated below) on perforated and/or porous substrates, like porous plastic films; fibrous substrates, both woven and non-woven; and in particular on perforated plastic films, both with a bidimensional or a tridimensional structure, that are among the most difficult substrates to be firmly and correctly bonded, as it is well known by all persons averagely skilled in the Science of hot-melt adhesives. Said optimum adhesiveness even on substrates that have holes or pores, and especially on perforated plastic films, both with a bidimensional or a tridimensional structure, as it will be better illustrated later, can be related to the very low initial crystallinity of the hot-melt adhesive formulations according to the present invention; and to the other characteristics deriving from this, like their particularly low setting speed from the molten state; the low speed by which the rheological parameter Tan Delta decreases during the solidification from the melt; and a sufficiently long open time.

an optimum processability in a wide range of application processes, even at high line speed, thanks to their low viscosity in the molten state and at relatively low processing temperatures—indicatively between about 150° C. and about 180° C.—so that they can be used even on thermosensitive substrates, for example plastic films that have low melting points or low temperatures of thermal deformation and/or on particularly thin substrates, like e.g. plastic films or nonwovens having a very low basis-weight.

A very low or even null level of low molecular weight additives, like especially traditional liquid plasticizers (as mineral oils and poly-butene oils) and also tackifiers, with consequent significant advantages in terms of absence of malodors, as well as absence of demixing and resultant slow migration of said low molecular weight compounds out of the adhesive itself, and so on.

It's opportune to emphasize that this very low or even null levels of low molecular weight additives, like tackifiers and hydrocarbon plasticizing oils, give also additional important advantages. For example it is well known that e.g. tackifiers are synthesized from complex blends—whose detailed composition is often at least partially undetermined/unknown—of various hydrocarbon monomers of different petrochemical or natural origin (e.g. isoprene, piperylene, limonene and other terpenes, phenol, indene, coumarone, styrene and its derivatives, abietic acid and its derivatives, various cyclic and polycyclic compounds etc.). These complex blends of different monomers generally leave, in the final tackifiers, traces of unreacted monomers that can cause, besides problems of malodors, also serious problems of toxicity, sensitization/allergenicity, and so on. In a preferred embodiment of the present invention, when it is anyhow deemed opportune to add a low level of tackifiers to the hot-melt adhesive formulations of the present invention, are strongly preferred tackifiers that have a particularly low level of Volatile Organic Compounds (VOC), i.e. of residual monomers, solvents etc. like the ones supplied with the acronym LV (Low Volatiles) in their commercial trademarks by Eastman (USA).

An ability of significantly varying, in the solid state and with aging in time at room conditions, over a few days after their application, both their level of crystalline content as well as some essential rheological parameters, especially their Elastic Modulus G' and their Tan Delta. More specifically while in the initial conditions of application and bond formation, both crystallinity and G' are low, while Tan Delta is relatively high, so to maximize the initial tackiness, wettability and contact area and therefore the initial adhesive strength, the same parameters slowly vary in time and reach a final stable value in about seven days, further increasing to higher values the already good initial adhesiveness and cohesion at Time Zero. In particular this further improvement with aging of adhesive strength and of cohesion occurs thanks to a significant increase, during aging, both of the crystalline content and of the Elastic Modulus G' of the present hot-melt adhesive, accompanied by a simultaneous decrement in their Tan Delta.

It is moreover opportune to underline that some of these characteristics and properties, all of them highly desirable in a hot-melt adhesive formulation, and that are present in the adhesive formulations according to the present invention, are often mutually contradictory one versus the other. For example the contemporary presence of a low viscosity in the molten state and of an excellent initial cohesion in the solid state; the contemporary presence of a low viscosity and of a very good processability in the molten state even by using very low or even null levels of low molecular weight additives, like tackifiers and/or plasticizers; an optimum cohesion combined with a solidification rate from the molten state that is particularly slow and/or with sufficiently long open times, and so on.

WO2015/095 480 discloses a holt melt adhesive material and articles made using the hot melt adhesive to assemble structures in an article. The adhesive material tipically is manufactured by blending two compatible amorphous polymers.

US2007/281118A1 discloses a hot melt adhesive composition, including an amorphous poly-alpha olefin, an amorphous propylene/butene copolymer, a grafted polyethylene, and a wax. The hot melt adhesive composition can be used for bonding woven polypropylene substrates.

U.S. Pat. No. 6,872,279 discloses a sprayable hot melt adhesive composition, including 30-70 wt. % of one or more poly-alpha-olefins, 5-30 wt. % of at least one oil, and 20-60 wt. % of at least one hydrocarbon resin having a softening point ranging from 70 to 140° C.

SUMMARY OF THE INVENTION

The problem that the present invention intends to solve is to formulate hot-melt adhesives, processable also in high speed processes, for example not lower than about 200 m/minute and preferably not lower than about 300 m/minute, that show at the same time a low viscosity in the molten state as well as a low application temperature, combined with a strong cohesion in the solid state and a strong adhesiveness even at "time zero", i.e. just after their application and solidification from the molten state, especially on substrates that are particularly difficult to be strongly bonded, like perforated plastic films, both with a bidimensional or a tridimensional structure, and in general o other similar plastic substrates that have holes, voids or pores, like fibrous substrates, porous films, and the like, said substrates being especially used for the manufacturing of absorbent hygienic articles. Furthermore the already good initial adhesiveness and cohesion of said hot-melt adhesives can be further improved by aging in time, because said aging causes a significant increase in their crystallinity and Elastic Modulus G' and a simultaneous decrease in Tan Delta.

This problem is solved by an adhesive composition having the characteristics of Claim 1), by a bonded structure having the characteristics of Claims from 35) to 37), by an article having the characteristics of Claims from 38) to 41) and by an article having the characteristics of Claims from 42) to 44). The other sub-claims disclose preferred embodiments.

DETAILED DESCRIPTION OF THE PREFERRED EMBODIMENTS AND MAIN PROPERTIES OF THE ADHESIVES ACCORDING TO THE PRESENT INVENTION

The adhesive hot-melt formulations according to the present invention comprise, as their main or even unique polymeric component, at least a polymer composition composed by two polyolefins, that are substantially non-stereospecific, as shown by their low value of Crystallization Enthalpy from the molten state, and that have Number average Molecular Weights Mn such to differ for no more than about 6,000 g/mole, being their single Number average Molecular Weights Mn of the two single polyolefins comprised between about 3,000 g/mole and about 30,000 g/mole.

In another embodiment of the present invention, said two polyolefins have Mass average Molecular Weights Mw comprised between about 15,000 g/mole and about 200,000 g/mole, being also selected in such a way that their single Mass average Molecular Weights Mw differ for not more than about 15,000g/mole.

Said two polyolefins, that are substantially non-stereospecific, are present in the polymer composition in a ratio by weight that can vary from about 1:20 and about 20:1.

The hot-melt adhesive formulations according to the present invention show a particularly low initial crystallinity at time zero, as highlighted by their low Crystallization Enthalpy from the molten state, that is not higher than about 12 J/g, when measured, in a decreasing temperature DSC test from the molten state, at the cooling rate of 1° C./minute, according to the DSC test method that will be illustrated in details below.

Moreover the present adhesive formulations, during their application from the molten state, show also a peculiarly slow solidification rate; in particular they show a Solidification Rate around their Rheological Setting Point (see below for the definition and the measurements of these parameters) typically not greater than about 5,000 Pa/° C.; and they show also, during their solidification, a Decreasing Speed of their rheological parameter Tan Delta, still around the same setting point, that is typically not greater than about 0.5 (° C.)$^{-1}$.

As it will be better illustrated in the following paragraphs, said variation speeds (very slow and controlled) of said two rheological parameters during their application from the melt, make the hot-melt adhesive formulations according to the present invention particularly suitable for strongly bonding substrates that have openings, holes, voids or pores, both macroscopic and microscopic, like porous plastic films, fibrous substrates, both woven and non-woven, as well as perforated plastic films, both with a bidimensional or a tridimensional structure, all said mentioned substrates being especially used, for example, for the manufacturing of absorbent hygienic articles.

The hot-melts adhesive formulations according to the present invention show, besides an optimum processability even in application processes at high line speed, also an unexpected combination of positive properties, that are highly desirable in a hot-melt adhesive. In particular:

They have low viscosities in the molten state which property, besides justifying their optimum processability even in high speed processes, allow to apply these formulations at relatively low temperatures on thermosensitive substrates, for example plastic films that have low melting points or low temperatures of thermal deformation and/or on particularly thin substrates, like e.g. plastic films or nonwovens having a very low basis-weight.

At the same time, said formulations show excellent properties of initial high cohesion (a characteristic generally incompatible with a low melt viscosity of a hot-melt adhesive) and high initial adhesiveness on polymeric substrates like plastic films or non-wovens made of plastic fibers.

Moreover, said very good initial values of adhesive strength and cohesion, further improve with time, thanks to an increase, during aging in the solid state at room conditions, of their levels of crystallinity, of their Elastic Modulus G' and thanks to a contemporary decrease in the value of their Tan Delta.

As well known to every person averagely expert in the Science of Adhesion, if the adhesive bond has already, since its initial conditions of formation, a sufficiently high adhesive strength, and a sufficiently high cohesion, this increase by aging on longer times of G', of the crystallinity level, as well as the decrease in the values of Tan Delta contribute to further increase both the adhesive strength and the cohesion.

If, on the contrary, the adhesive bond was, since time zero, excessively weak, for example because the adhesive was not sufficiently tacky or was unable to wet sufficiently large areas of the substrate, it is obvious that even a further crystallization, an increase in G' and a decrease in Tan Delta on longer times, are unable to significantly increase the too weak initial adhesive strength.

In fact, if e.g. the contact area between the adhesive and the substrate is insufficient and too small, it will continue to remain in the same conditions for ever. Therefore the global adhesive strength, that anyhow is directly proportional to said contact area, will continue to show unacceptably low values, even when the adhesive, per se, might increase somehow with time its level of crystallinity or its Elastic Modulus and decrease Tan Delta.

It is also worthy to highlight that the articles in which the adhesive formulations of the present inventions are preferably used, i.e. absorbent hygienic articles, arrive to the final user/are used, typically after a few months, e.g. at least two or three months, after their manufacturing. It is therefore evident that the adhesive properties that are of main interest for the final user, e.g. the adhesive "peel strength" (see later), are those that can be measured in "aged conditions", according to the previously given definition.

In a preferred embodiment, the hot-melt adhesive formulations according to the present invention are substantially free from polymeric or oligomeric compounds, deriving from monomers different from mono-olefins from C2 to C6, and in particular are substantially free from poly-unsaturated monomers, that may be linear, cyclic, poly-cyclic and in general heavier than C6, whose residues may have possible toxic, sensitizing and/or allergenic effects, like for example isoprene, piperylene, limonene and other terpenes, phenol, indene, coumarone, styrene and its derivatives, abietic acid and its derivatives, various cyclic and polycyclic compounds, etc.

Moreover, in another preferred embodiment, of the present invention, when it is anyhow deemed opportune to add some tackifiers to the hot-melt adhesive formulations of the present invention, are strongly preferred tackifiers that have a particularly low level of Volatile Organic Compounds (VOC), i.e. of residual monomers, solvents etc. as illustrated in more details later.

According to the present invention, it has been surprisingly discovered that it is possible to achieve all the previously described highly desirable characteristics of a hot-melt adhesive, by using, as the main or even unique polymeric basis of said adhesives, a polyolefinic polymer composition, that is formed by at least two polyolefins, having a substantially non-stereospecific structure, and therefore an initial crystallinity that is peculiarly low, said polyolefins having not too high molecular weights and chosen so that the difference between the modes of their single molecular weights distributions is not greater than a sufficiently small value.

This selection criterion of the two composing polyolefins, gives to the resulting polymer composition a peculiar and highly beneficial molecular weight distribution, with a configuration that is broadened compared to the original single distributions and that has a bimodal structure.

Moreover, because in this way are made available significant fractions both of low and high molecular weights, more than it would be possible by utilizing a single polyolefinic polymer, it is possible to balance and to optimize both a good initial adhesiveness (that can be correlated to the fraction of low molecular weights and to the low initial residual crystallinity) and a good initial cohesion (that can be correlated to the fraction of high molecular weights, which fraction however, being present in controlled percentage, doesn't cause excessive viscosities in the molten state).

An initial crystallinity of the present hot-melt adhesive formulations that is particularly low, in turn causes further peculiar rheological properties, like first of all a Solidification Rate from the molten state, around the Rheological Setting Point, that is particularly slow and also a Decreasing Rate of Tan Delta, in the same conditions, that is also particularly slow.

As it will be better explained more in detail below, these two rheological properties during the application from the melt contribute to achieve excellent initial adhesive strength, especially on substrates that have holes, voids or pores, like perforated plastic films, fibrous substrates or porous plastic films.

All this set of highly beneficial properties, that cause at the same time high initial adhesiveness, optimum initial cohesion and low viscosity in the molten state, allow to avoid most of the gravest problems that are present in the greatest part of the existing Prior Art.

In particular:

They avoid the need to include into the formulations other polymers that have high molecular weights and high crystallinity, like polyolefins at high tacticity, crystalline polyolefinic elastomers and the like, that—besides unacceptably increasing the viscosity in the molten state and consequently the possible application temperature of the adhesive—make much quicker the solidification from the molten state in the moment when the adhesive bond is formed, in this way worsening the wettability of the substrate; significantly increase the initial hardness of the adhesive; decrease its tackiness and negatively influence its open time.

Still owing to analogous reasons and again differently from what is taught by a large part of the Prior Art, the hot-melt adhesive formulations according to the present invention can in case use only very small quantities or even null quantities, of compounds at low molecular weight and very high crystallinity, like typically waxes.

They make also useless or limit to a minimum the need to add compounds at low molecular weight, used for increasing the adhesiveness or the tackiness of hot-melt adhesives, like tackifiers, or liquid plasticizers at low viscosity, as mineral oils, poly-iso-butylene oils and the like.

In this way it is possible to avoid malodors, that are typical of most tackifiers, besides several other well known problems that derive from the massive use of low molecular weight additives, like a possible demixing in time of the compounds from the rest of the adhesive and their slow migration even outside of the adhesive itself. Furthermore in this way are avoided also possible problems of toxicity or sensitization and allergenicity, that (especially in tackifiers) are due to residues of unreacted poly-unsaturated monomers, linear or cyclic and in general heavier than C6, that can notoriously have toxic or sensitizing and/or allergenic effects.

Detailed Discussion of the Main Properties of the Adhesives According to the Present Invention The Polymer Composition Having a Broadened and Bimodal Distribution of Molecular Weights As mentioned above, the polymer composition, at low initial crystallinity, formed by two non-stereospecific polyolefins, that is the main or even the unique constituent of the hot-melt adhesive formulations according to the present invention, shows a distributions of molecular weights that is broadened in comparison to the two original single distributions of the two polyolefins and that has a bimodal structure.

These characteristics give to the hot-melt adhesives that comprise this type of polymer compositions, a combination of novel peculiar properties, like low viscosity in the molten state, high initial adhesiveness and cohesion, especially on substrates that have holes, voids or pores. This combination of novel peculiar properties cannot be obtained inside the same adhesive, if one utilizes blends of two or more polymers that have very different characteristics one versus the other, like polymers at low crystallinity blended with polymers at high crystallinity, or polymers at very low molecular weight blended with polymers at very high molecular weight, as taught from the Prior Art.

In particular, the beneficial and surprising results of the present invention are obtained by selecting the two non-stereospecific polyolefins, that form the polymer composition comprised in the adhesives of the present invention, according to the criteria that are described below and by blending said two polyolefins in a ratio by weight that is comprised between about 1:20 and about 20:1.

Said non-stereospecific polyolefins have both a quite low initial crystallinity, as revealed by their low initial Crystallization Enthalpies, measured by DSC (Differential Scanning Calorimetry), at the cooling rate from the molten state of 1° C./minute, according to the test method that will be described in all details below, said initial Crystallization Enthalpies of the single polyolefins being not greater than about 20 J/g, preferably not greater than about 15 J/g and more preferably not greater than about 10 J/g.

In a first preferred embodiment of the present invention, said non-stereospecific polyolefins have Number average Molecular Weights Mn comprised between about 3,000 g/mole and about 30,000 g/mole and they are selected so that the difference between the Number average Molecular Weights of the two polyolefins is not greater than about 6,000 g/mole, preferably not greater than about 5,000 g/mole, and more preferably not greater than about 3,000 g/mole and even more preferably not greater than about 2,500 g/mole.

In a second preferred embodiment of the present invention, said non-stereospecific polyolefins have Mass average Molecular Weights Mw comprised between about 15,000 g/mole and about 200,000 g/mole and the two polyolefins are selected so that the difference between their Mass average Molecular Weights is not greater than about 15,000 g/mole, preferably not greater than about 12,000 g/mole and more preferably not greater than about 10,000 g/mole.

If the modes of the two distributions of molecular weights of the two constituting polyolefins are too different one from the other, their blend has a distribution of molecular weights with two peaks that are totally separated and distinct, and the blend behaves according to the separate addition of the "single" properties of each single polyolefin; in particular e.g. the blend can even show a very fast speed of solidification from the melt, that is typical of the polymer fraction with the highest molecular weights, combined with a low initial cohesion, that is typical of the polymer fraction with the lowest molecular weights.

If on the contrary the two modes of the distributions of molecular weights of the two polyolefins are relatively close one to the other, their blend generates a new polymer composition in which most parts of the two distributions of molecular weights merge one into the other and overlay, keeping still two separate modality peaks (bimodality), but inside one single curve of distribution of molecular weights, curve that has a broadened configuration, much broader than it could be possible to obtain by using just one polyolefin.

This peculiar structure gives to said polymer composition properties, such as a solidification rate and an initial cohesion, that are, in a certain sense, "reduced" compared to a blend of polyolefins with too different molecular weights; but both of them reduced in a positive direction, by decreasing, from one side, the solidification rate, without, from the other side, losing a sufficient initial cohesion.

Moreover, this excellent compatibility and homogeneous behavior of the polymer composition described in the present invention, is further favored if the two constituting polyolefins, besides having average molecular weights that are selected according to the above mentioned criteria and besides having a common low initial crystallinity/stereospecificity, have also, preferably, a substantially similar chemical composition.

It has been also surprisingly discovered that the polymer composition, comprised into the adhesives of the present invention, has generally an initial crystallinity (as revealed by the initial Crystallization Enthalpies) that in most cases is even lower than the weighted average value of the already low initial crystallinities of the two single composing polyolefins, which fact makes even more beneficial the use of said polymer composition rather than of the single polyolefins.

Without depending for this from any theory, one could reasonably think that the blending of the two polymers, which are structurally and chemically similar, but not identical, and the presence of a molecular weight distribution that is significantly broadened in comparison with the ones of the single polymers, may generate further "disturbs" and slow-down in the initial crystallization from the melt, which cause a further decrease in the already low initial crystallinity of the polymer composition compared to the one of the single constituents. As a support for this possible explanation, one could refer to what is written in the book "Crystallization of Polymers", edited by Marcele Dosiere, for example at page 26 and the following pages, book that is herein incorporated as a reference, about the relationship between the level of crystallinity that can be typically achieved in a polymeric system and the molecular weights and their distributions in such a system.

Examples of non-stereospecific polyolefinic polymers that can be used as constituents for the above described polymer composition, are e.g. the polyolefinic polymers sold under the trade marks Rextac RT and Rextac E by Rextac (USA); the ones sold under the trade mark Vestoplast by Evonik (Germany); the ones sold under the trade mark Eastoflex by Eastman (USA); the ones sold under the trade marks Koattro, Polybutene-1, PB, PBM and DP by Lyondell Basell (The Netherlands), and the like.

In a preferred embodiment of the present invention, the above described polymer composition, that is comprised into the hot-melt adhesive formulations according to the present invention, has a Melt Flow Rate (MFR) comprised between about 10 dg/minute and about 6,000 dg/minute, preferably comprised between about 200 dg/minute and about 5,000 dg/minute, when measured according to the test method ISO 1133 at 190° C. and under a load of 2.16 kg.

In a second preferred embodiment, said polymer composition has a melt viscosity, as measured according to the test method ASTM D3236-88 at 190° C., comprised between about 200 mPa·s and about 500,000 mPa·s, preferably between about 400 mPa·s and about 100,000 mPa·s.

In the hot-melt adhesive formulations according to the present invention, said polymer composition is present from about 30% by weight to about 100% by weight of the hot-melt adhesive formulation, preferably from about 50% by weight to about 97% by weight and more preferably between about 60% by weight and about 95% by weight.

The Hot-Melt Adhesive Formulations According to the Present Invention

The hot-melt adhesive formulations according to the present invention, that comprise, as their main or unique polymeric constituent, the above described polymer composition, are furthermore characterized by the main properties that are described below in details.

Said formulations preferably comprise polymeric and oligomeric compounds that exclusively derive from notoriously non-toxic mono-olefins from C2 to C6, like ethylene, propylene, butene-1 and hexene. In fact in this preferred embodiment, the hot-melt adhesive formulations according to the present invention are substantially free from any polymeric or oligomeric compound, synthetic or natural, that derives from monomers or blends of monomers different from the above mentioned mono-olefins from C2 to C6.

A typical example of these not preferred compounds, especially if present at the usual high levels disclosed by most of the Prior Art, are tackifiers. In fact tackifiers are synthesized or are composed by complex mixtures, very often not known in all the elements of their detailed composition, of various monomers derived from petro-chemical or natural sources (e.g. isoprene, piperylene, limonene and other terpenes, phenol, indene, coumarone, styrene and its derivatives, abietic acid and its derivatives, various cyclic and polycyclic compounds etc.) that generally continue to be present in unreacted traces and that, besides causing problems of malodors, can cause also serious problems of toxicity, sensitization, allergenicity and the like.

The hot-melt adhesive formulations according to the present invention have a very low initial crystallinity, as revealed by their very low initial Crystallization Enthalpy from the molten state, measured by DSC (Differential Scanning calorimetry), at the cooling rate of 1° C./minute (according to the test method that will be illustrated below in all details), that is not greater than about 12 J/g, preferably not greater than about 10 J/g and more preferably not greater than about 8 J/g. The use, in this DSC test, of a particularly slow cooling rate as 1° C./minute, makes this test highly significant, because it well reproduces the real phenomena that happen during the application onto the substrate of the molten adhesive and its slow spontaneous cooling and solidification during the formation of the adhesive bond.

In a preferred embodiment, the initial Crystallization Enthalpy of the hot-melt adhesive formulations according to the present invention is not greater than the weighted average value of the two initial Crystallization Enthalpies of the two single non-stereospecific polyolefins that are comprised in said formulations.

Moreover the present hot-melt adhesive formulations are characterized, during their application from the molten state, by three initial rheological parameters:

1) A Solidification Rate from the molten state, around their Rheological Setting Point and as a function of decreasing temperature, that is particularly slow and that is not greater than about 5,000 Pa/° C., preferably not greater than about 3,000 Pa/° C. and more preferably not greater than about 2,000 Pa/° C.

2) A slow Decreasing Rate of Tan Delta, still around their Rheological Setting Point and again as a function of decreasing temperature, that is not greater than about 0.5 (° C.)$^{-1}$, preferably not greater than about 0.1 (° C.)$^{-1}$ and more preferably not greater than about 0.08 (° C.)$^{-1}$.

3) Said Rheological Setting Point being preferably comprised between about 40° C. and about 100° C. and preferably between about 45° C. and about 90° C.

These three initial rheological parameters, during the application from the melt, represent in a significant way the range of temperatures and the modalities, around the rheological setting point, in which a hot-melt adhesive, applied in the molten state on a substrate, forms with it an adhesive bond, while it spontaneously cools and solidifies.

Without for this depending from any theory, the correlations between the initial chemical, structural and rheological characteristics of the present hot-melt adhesive formulations and the optimum initial adhesive strength and cohesion that is observed in the bonding of various substrates, but especially of substrates having holes, voids or pores, may be reasonably explained according to what is illustrated below.

It is important to emphasize that the above mentioned types of substrates are particularly difficult to be strongly bonded for various reasons. In particular:

Their reduced contact area between the adhesive and the substrate, due to the presence of the holes or voids themselves. This "missing contact area", due to the holes or voids, can even be equal to about 50% of the total area of the perforated substrate;

The consequent need for the adhesive to be able to partially penetrate inside said holes or voids, in this way maximizing the contact area and also creating a strong mechanical entanglement between the adhesive and the substrate, said entanglement being able to optimize (and often in a significant way) the overall initial adhesive bonding strength. In fact, as already mentioned, the observed global adhesive strength is the sum of the strength of these mechanical entanglements between the adhesive and the substrate (mechanical component of the adhesion) plus the pure "chemical component" of the adhesive strength, due to the interaction forces existing between the molecules of the adhesive and the molecules of the substrate (Van der Waals forces, dipole forces, hydrogen bonds etc.);

The very frequent need to avoid—in the bonding of said substrates—the application of any pressure/counter-pressure, that would destroy their tridimensional structure (when present); that would compact and stiffen them (for fibrous substrates) and that might risk of pushing the still partially fluid adhesive too deeply inside the perforated, fibrous or porous substrate, in this way removing a substantial fraction of the adhesive from the surface area that needs to be bonded and therefore causing a significant decrease of the overall observed initial adhesive strength.

It is therefore necessary that, around its solidification point, in the critical moment when the adhesive bond is formed, the adhesive formulation is able to remain as long as possible "soft" and tacky; and that it is able also to spontaneously flow, as long as possible, in this way partially penetrating inside possible holes, voids or pores, even without applying any external compression.

First of all, as a consequence of the peculiar distribution of the molecular weights of the polymer composition comprised in the present adhesives, distribution that has a broadened configuration and a bimodal structure, it is possible to reasonably think that, once that the molten adhesive formulations according to the present invention are coated on the substrate that must be bonded, while the fraction of the polymer composition gathered around the first center of modality at the higher molecular weights, solidifies first, giving an optimum initial cohesion, the remaining fraction of the polymer composition, formed by the lowest molecular weights and gathered around the second center of modality with the lower molecular weights, continues to remain for some time in a fluid state and continues to flow, to wet and to even partially penetrate the substrate, in this way optimizing the overall strength of the formed adhesive bonds.

These phenomena are well represented by the two rheological parameters Solidification Rate around the Rheological Solidification Point; and Decreasing Rate from the melt of Tan Delta, around the same point.

The first parameter, the Solidification Rate, is determined (according to the test method that is described below) by measuring the rate by which, around the solidification point/temperature, the rheological parameter Elastic Modulus G' (that, as well know, represents the "solid character" or also the "hardness" of whichever substance) increases as a function of the decrease in temperature, due to the adhesive's spontaneous cooling and solidification from the melt and the contemporary formation of the bond between adhesive and substrate.

The slower is the increase of G', at an equal variation of decreasing temperature, the longer is the time during which the adhesive formulation remains soft, tacky and therefore able to create stronger adhesive bonds. In an analogous way, as well known by every person averagely expert in Rheology and in the Science of Adhesives, for all substances the dimensionless rheological parameter Tan Delta is proportional to the ability of the substance itself to spontaneously flow and to wet increasing areas of a possible substrate.

By definition, above its own Rheological Setting Point (or Rheological Setting Temperature) a thermoplastic substance has its Tan Delta greater than 1 (i.e. it is "rheologically liquid"); and below said point/temperature, it has its Tan Delta lower than 1 (i.e. it is "rheologically solid").

However, if the rate by which Tan Delta, during the application and solidification from the melt, decreases with the decreasing of temperature is slow, this means that the material remains for a longer time able to flow (in part even slightly below its setting point), in this way being able to contact and wet larger areas of the substrate; and if holes or voids are present, the fluid or semi-fluid adhesive is able also physically partially penetrate at a higher level inside the substrate itself. Thanks to this, the overall initial adhesive strength is maximized, because both the contact area between the adhesive and the substrate is maximized, as well as because this partial penetration into the substrate creates mechanical entanglements between the adhesive and the surface roughness, the holes, the voids or the fibers of the substrate itself.

Also these two initial rheological parameters are determined (as it will be illustrated in more details below) in a test, done under decreasing temperature, starting from the molten state, and at a particularly slow cooling rate, equal to 2° C./minute. These experimental conditions once again allow to mimic, in a very significant way, the real phenomena that occur during the coating of the molten adhesive onto the substrate, its following slow spontaneous cooling, its solidification and the contemporary creation of the adhesive bond.

It is however crucial to emphasize that the particularly low values of these important initial rheological parameters, measured around the Rheological Setting Point of the adhesive (that means in an opportune interval of temperatures slightly above and slightly below the Crossing Temperature of the two rheological moduli, in the field of temperatures above room temperature), in order to practically optimize the strength and the usefulness of the adhesive bonds created in such a way, cannot disregard absolute limits for said solidification temperature (or Rheological Setting Point).

In fact hot-melt adhesive that have Rheological Setting Points that are too high, for example higher than about 100° C., could be processed and applied only at excessively high temperatures. Actually, as it is well known to every person averagely expert in the processing of hot-melt adhesives, the optimum temperatures for processing hot-melt adhesives generally fall in a range positioned about +80° C. and about +120° C. above their Rheological Setting Point.

On the other side, adhesives that have too low Rheological Setting Points, for example riskily close to room temperature, might potentially have serious problems in their use, because the adhesive might spontaneously "collapse", e.g. in warm climates, because of its excessive softening at too low temperatures.

For these reasons, the adhesive formulations according to the present invention preferably have a Rheological Setting Point comprised between about 40° C. and about 100° C. and more preferably between about 45° C. and about 90° C.

The hot-melt adhesive formulations according to the present invention have an excellent processability even at relatively low temperatures and even in processes at high line speed, thanks to their low melt viscosity. In particular, in a preferred embodiment, they have a Brookfield viscosity at 170° C., measured according to the test method ASTM D3236-88, that is not greater than about 6,000 mPa·s, preferably not greater than about 5,500 mPa·s. In a second embodiment, they have a Brookfield viscosity at 150° C., measured according to ASTM D3236-88, that is not greater than about 10,000 mPa·s, preferably not greater than about 9,500 mPa·s.

Moreover, in another preferred embodiment, said formulations have a shear viscosity at very high shear rate, measured e.g. by a Capillary Rheometer, that is also low; in particular they show a shear viscosity at 160° C. and at the shear rate of 100,000 $(s)^{-1}$ that is not higher than 650 mPa·s, and preferably not higher than 500 mPa·s. As well known to every person averagely expert in the science of processing hot-melt adhesives, said shear viscosity measured at very high shear rates, like e.g. at 100,000 $(s)^{-1}$ and at a typical processing temperature, like 160° C., well reproduces the conditions of processing of a holt-melt adhesive in processes at high line-speed, as for example are met on industrial lines for the manufacturing of hygienic absorbent articles. Therefore the low shear viscosity at such very high shear rate assures that the hot-melt adhesive formulations according to the present invention show an excellent processability even on industrial lines operated at high speed like typically 250 m/minute or above.

The possibility that the adhesive formulations disclosed herein can be very well processed even at relatively low temperatures, is also expressed by their preferred values for another thermal parameter, i.e. the parameter known as Ring & Ball Softening Point, measured according to the test method ASTM D36-95. The hot-melt adhesive according to the present invention have Ring & Ball Softening Point, at time zero, that preferably is not greater than about 130° C. and more preferably is not greater than about 125° C.

Moreover, the remarkable ability of the present adhesive formulation of remaining—in contrast with what taught by the Prior Art—softer and tackier, for significantly longer time, during their cooling from the molten state and the creation of the adhesive bond, is demonstrated also by the rather initial high value that they have for a further parameter that is also well known to every person averagely expert in hot-melt adhesives as a reliable measure of the adhesiveness, softness and tackiness of a certain adhesive, i.e. its so called "Needle Penetration", measured at 55° C. according to the test method ASTM D1321-04. The hot-melt adhesive formulations according to the present invention have a Needle Penetration at 55° C. and at time zero, that is not lower than about 40 dmm and preferably not lower than about 60 dmm.

The hot-melt adhesive disclosed herein have also a relatively long Open Time, another parameter that well expresses that initial prolonged tackiness that facilitates a strong initial adhesiveness in a broad range of processes at various line-speeds.

However, for the preferred bonding of substrates that have holes, voids or pores, like in the present case, the Open Time cannot be indefinitely long. In fact adhesives that remain permanently tacky (i.e. that have an "infinitely long" Open Time), if used inside absorbent hygienic articles, might come in accidental contact with the skin of the wearer, through the holes and openings of the perforated or fibrous substrates, causing in this way serious discomfort and possible inconveniences. Or also, if the construction adhesives of such an absorbent hygienic article remain tacky for a too long time, the article itself—that inside its package is subjected to pressure—might undergo undesired gluing between different components that should not adhere one to the other, inside the same article, or undergo permanent deformations of their structures, and so on.

For said reasons, the present hot-melt adhesive formulations have preferably an Open Time that is comprised between about 1.5 minutes and about 600 minutes, and more preferably is comprised between about 2 minutes and about 300 minutes. Said Open Time is measured according to the test method ASTM D4497-94, opportunely modified according to what illustrated below.

As already mentioned, the hot-melt adhesive formulations according to the present invention have also the ability, over aging in the solid state at room conditions, to further increase the already excellent initial adhesive strength and cohesion of the formed bonds. These phenomena essentially occur thanks to the following spontaneous variations with time at room temperature of three main physical characteristics of the present hot-melts:

An increase with time of their level of crystallinity at 23° C. This increase can be assessed e.g. by comparing the values of the initial Crystallization Enthalpy from the melt (that is proportional to the initial crystalline content) with the Crystalline Enthalpy of the same aged solid material, measured again by DSC as a melting peak, during a heating cycle at the same heating rate of 1° C./minute (see later for a detailed description of the test method);

An increase with time of their Elastic Modulus G' in the solid state and at room temperature. Said increase can be assessed for example by measuring, with the test method illustrated in details below, the value of G', at the temperature of 23° C. and at the deformation frequency of 1 Hz, first on the adhesive "at Time Zero", i.e. at a time not longer than 120 minutes from its solidification from the melt; and then, in the same test conditions and on the same adhesive, after that it has been aged for seven days at 23° C. and 50% Relative Humidity;

A decrease with time of their Tan Delta in the solid state and at room temperature. Also, this variation between the initial and aged values of Tan Delta can be measured in the same rheological test of the previous point, used for assessing the initial and aged values of the Elastic Modulus G'.

More specifically, in a preferred embodiment, the hot-melt adhesive formulations according to the present invention, have a Crystalline Enthalpy after aging, measured by DSC as melting Enthalpy with a heating cycle on aged samples, from 23° C. to 180° C. at a heating rate of 1° C./minute, that is increased, in comparison with their initial Crystallization Enthalpy from the melt of at least about 50%, preferably of at least about 65% and more preferably of at least about 75%.

In an additional preferred embodiment, the present hot-melt adhesive formulations, after aging for seven days at 23° C. and 50% Relative Humidity, show an increased Elastic Modulus G', measured at room temperature and at the frequency of 1 Hz, in comparison with their G' at Time Zero, measured again at 23° C. and 1 Hz. In a first sub-embodiment the aged Elastic Modulus G', at 23° C. and 1 Hz, shows a percent increase towards the correspondent Elastic Modulus G' at Time Zero, that is not lower than about 50%, preferably not lower than about 60% and more preferably not lower than about 70%. In a second sub-embodiment the aged Elastic Modulus G', at 23° C. and 1 Hz, of the present formulations has an absolute value not lower than about 1.3 Mpa, preferably not lower than about 1.5 MPa and more preferably not lower than about 1.6 MPa.

In a similar further preferred embodiment, the hot-melt adhesive formulations according to the present invention, after aging for seven days at 23° C. and 50% Relative Humidity, show a decreased Tan Delta, measured at room temperature and at the frequency of 1 Hz, in comparison with their Tan Delta at Time Zero, measured again at 23° C. and 1 Hz. In a first sub-embodiment the aged Tan Delta, at 23° C. and 1 Hz, shows a percent decrease towards the correspondent Tan Delta at Time Zero, that is not lower than about 30%, preferably not lower than about 35% and more preferably not lower than about 40%. In a second sub-embodiment the aged Tan Delta, at 23° C. and 1 Hz, of the present formulations has an absolute value not higher than about 0.4, preferably not higher than about 0.3 and more preferably not higher than about 0.28.

The above illustrated variations of the crystalline content and of the main rheological parameters of the hot-melt adhesive formulations according to the present invention, when aged at room conditions, well mimic the variations occurring inside said adhesives, once that they are applied inside a hygienic absorbent article, during the warehouse storage of said articles before their sale and use.

It is however of interest to consider that, during the use of the hygienic article on the body of the user, the adhesives have also to withstand, for the time of use, i.e about a few hours, the body temperature of 37° C.; i.e. at this temperature they must in particular not to soften and become too mechanically weak. Therefore it is also of interest in these preferred hygienic applications for the present adhesives, that they show also a sufficiently high absolute value of their Elastic Modulus G' at 37° C. that expresses their "solid character" even at this relatively high temperature. As well known to the averagely expert person in the Science of Rheology and Adhesives, in said use these adhesives are mainly subjected to a stress under creep; and an adequate resistance to this type of stress is well represented by a sufficiently high value of the Elastic Modulus G', measured of course at 37° C. but at the frequency of 0.01 Hz.

Therefore in a further preferred embodiment, the hot-melt adhesive formulations according to the present invention have an aged Elastic Modulus G', measured at 37° C. and at the frequency of 0.01 Hz, that is not lower than about 30,000 Pa, preferably not lower than about 50,000 Pa and more preferably not lower than about 100,000 Pa.

All the above mentioned characteristics and properties concur to give to the hot-melt adhesive formulations of the present invention, both at Time Zero and even more in aged conditions, excellent adhesive strength and cohesion, even on difficult to bond substrates, like in particular perforated plastic films, fibrous substrates or porous plastic films.

In general, the present adhesive formulations are able to generate an aged Peel Adhesive Strength (measured according to the test method illustrated below) that is greater than about 0.25 N per 50 mm of width, when they are applied at a basis weight comprised between 0.5 g/m$^2$ and about 50 g/m$^2$, between two substrates of which at least one is a fibrous substrate or a porous plastic film or a perforated plastic film.

As an additional advantage, these particularly difficult to bond substrates, like perforated plastic films etc. with the present hot-melt adhesive formulations can be processed and strongly bonded even at very high line speeds. For example said substrates can be processed and strongly bonded at line speeds that are not slower than about 250 m/minute, and at this speed, if the present adhesives are e.g. applied at a basis weight comprised between about 5 g/m$^2$ and about 20 g/m$^2$, they are able to show an aged Adhesive Peel Strength that is not lower than about 0.5 N/inch (0.197 N/cm), preferably not lower than about 0.8 N/inch (0.315 N/cm) and more preferably not lower than about 1.0 N/inch (0.394 N/cm).

Possible Additional Constituents of the Present Hot-Melt Adhesive Formulations

The Polymeric Viscosity Modifier, that is Non-Solid at Room Temperature

In a preferred embodiment of the present invention, the hot-melt adhesive formulations disclosed herein comprise, in a percentage by weight that is smaller than the one of the above mentioned polymer composition, that forms their main polymeric constituent, also an additional polymeric constituent, that is a metallocenic polyolefin homopolymer or copolymer, derived from mono-olefins from C2 to C6, said second minor constituent being highly non-stereospecific, so that its Crystallization Enthalpy from the melt is not greater than about 2 J/g, preferably not greater than about 1 J/G and more preferably it is substantially equal to about zero (i.e. in the measure of its Crystallization Enthalpy, according to the method described below, it is not possible to detect any crystallization peak).

Said metallocenic polyolefinic homopolymer or copolymer, that is highly non-stereospecific and with a practically undetectable initial crystallinity, shows in addition the peculiar characteristic that, in spite of being a polymer, is at room temperature a "non-solid" material, where "non-solid" has a meaning according to the previously given definition for this term. It is therefore able to significantly "flow" even at room temperature. The blending, even in a relatively limited quantity, of this third peculiar homopolymer or copolymer with the above mentioned polymer composition, gives to the final hot-melt adhesive formulations of the present invention, at least two types of further beneficial properties:

It increases the ability of the final adhesive formulations to flow and wet the substrates, and also of even physically penetrate inside their holes, voids, pores or between their fibers, during the application of the melt adhesive;

Because these peculiar polyolefinic homopolymers or copolymers, that are highly non-stereospecific and that are non-solid at room temperature, appear, at low temperatures, as gelatinous masses at very high viscosity (for example indicatively greater than about 15,000 mPa·s even at 50° C.), but they quickly lose viscosity at higher temperatures at which generally hot-melt adhesives are processed (for example, they have viscosities typically not greater than about 500 mPa·s and preferably not greater than about 300 mPa·s at 150° C.; and viscosities typically not greater than about 200 mPa·s and preferably not greater than about 100 mPa·s at 190° C.), these additional polymeric constituents, at the high temperatures at which the present hot-melt adhesives are processed, work as very effective viscosity modifiers, by decreasing the viscosity of the molten final adhesive formulation, and significantly improving its processability and extrudibility even in application processes at high line speed, for example not slower than about 250 m/minute. In this way, by using said polymeric viscosity modifiers, this excellent processability and low melt viscosities are achieved without introducing those problems (e.g. possible de-mixing and migration outside the adhesive itself) that are typically showed by the traditional low molecular weight plasticizers, as mineral oils, poly-iso-butylene oils and the like.

In a preferred embodiment of the present invention, this third polymeric constituent, that is non-solid at room temperature, is a non-stereospecific metallocenic copolymer of propylene and ethylene, containing propylene as its main monomer in molar fraction.

In another embodiment of the present invention, said copolymer is modified with small quantities (typically lower than about 10% by weight and preferably lower than about 5% by weight) of maleic anhydride, that, as well known in the field of hot-melt adhesives, can be helpful for further positively influencing the overall adhesiveness.

The hot-melt adhesive formulations according to the present invention comprise from zero to about 35% by weight, preferably from zero to about 15% by weight and more preferably from zero to about 10% by weight of the above described polymeric viscosity modifier, that is non-solid at room temperature. Propylene-ethylene copolymers, non-solid at room temperature and that can be used in the present invention, are for example the metallocenic non-solid copolymers supplied by Clariant (Switzerland) under trademarks like PPA 330 and the like, even in their versions modified with small quantities of maleic anhydride.

Other Additional Constituents

Due to the above examined reasons, the hot-melt adhesive formulations according to the present invention, comprise small and preferably null quantities of other low molecular weight additional constituents.

These low molecular weight additives, that in most of the Prior Art are traditionally blended inside the hot-melt adhesive formulations, often at percentages even greater than the content of polymers, and that, on the contrary, are preferably avoided or used at very low levels in the present invention, are in particular tackifiers; waxes; traditional liquid plasticizers, as mineral oils, poly-iso-butylene oils (PIB), liquid esters, and the like.

Especially waxes, that are compounds at very high crystallinity, if added in too large quantities, as often taught by Prior Art, can introduce in the adhesive formulations of the present invention, an initial level of crystallinity that here is undesired, because it might seriously impair just some of their most desirable and beneficial properties.

In particular too high percentages of crystalline waxes, might strongly increase their initial crystallinity (high Crystallization Enthalpy at Time Zero), stiffening them too much at time zero and making them less tackier. Moreover waxes might significantly increase their Solidification Rate from the melt, their Decreasing Rate of Tan Delta and might unacceptably shorten their Open Times, all parameters that contribute to deteriorate their initial adhesiveness.

Tackifiers

The hot-melt adhesive formulations according to the present invention, preferably do not comprise tackifiers. As already illustrated, this is important not only for avoiding malodors or de-mixing with time of these low molecular weight additives; but it's even more important because tackifiers, both natural and synthetic ones, derive or are synthesized from complex mixtures, often unknown in their detailed composition, of various monomers derived from petro-chemical or naturals sources (e.g. isoprene, piperylene, limonene and other terpenes, phenol, indene, coumarone, styrene and its derivatives, abietic acid and its derivatives, various cyclic and polycyclic compounds etc.). These heavy monomers, that generally remain in unreacted traces, can cause not only problems of malodors but even serious problems of toxicity, sensitization, allergenicity, and the like.

In those embodiments in which, for whatever reasons e.g. for increasing even more the initial tackiness, it is judged opportune to add small quantities of tackifiers, the hot-melt adhesive formulations according to the present invention comprise no more than about 15% by weight, preferably no more than about 10% by weight, and even more preferably no more than about 5% by weight of a tackifier or of a blend of tackifiers having a Ring & Ball softening point comprised between about 5° C. and about 160° C.

Among all the possible existing families of tackifiers, well known in the field of hot-melt adhesives, the preferred ones are those families that are the most compatible with polyolefins. In general the tackifiers that may be in case comprised into the adhesive formulations of the present invention can be chosen among aliphatic hydrocarbon tackifiers and their fully or partially hydrogenated derivatives; the aromatic hydrocarbon tackifiers and their fully or partially hydrogenated derivatives; the aliphatic/aromatic hydrocarbon tackifiers and their fully or partially hydrogenated derivatives; terpene tackifiers, modified terpene tackifiers and their fully or partially hydrogenated derivatives; rosins, their esters and their fully or partially hydrogenated derivatives. Hydrocarbon tackifiers, both aliphatic, aromatic and aliphatic/aromatic, especially in the form of their fully hydrogenated derivatives, are particularly preferred because they have an optimum compatibility with the polyolefinic polymer compositions, with a bimodal structure, used as the main or even unique constituent in the hot-melt adhesives according to the present invention. Furthermore it has been discovered that the tackifiers possibly used in the adhesive formulations of the present invention have advantageously a Ring & Ball softening point not lower than about 80° C., preferably not lower than about 90° C. and more preferably not lower than about 100° C. In a preferred embodiment of the present invention, when it is deemed opportune to add a low level of tackifiers to the hot-melt adhesive formulations of the present invention, are strongly preferred tackifiers that have a particularly low level of Volatile Organic Compounds (VOC), i.e. of residual monomers, solvents etc. More precisely the preferred tackifiers for the hot-melt formulations of the present invention have a Volatile Organic Compound (VOC) value not higher than about 1,000 ppm, preferably not higher than 600 ppm and more preferably not higher than 300 ppm, as determined according to the standard test method VDA 278.

Traditional Liquid Plasticizers

Still for the above discussed reasons, the adhesive formulations according to the present invention do not comprise at all, or comprise at very low levels, traditional liquid plasticizers, at low molecular weight and viscosity, like, just to mention the most commonly used examples, mineral oils both paraffinic and naphthenic, vegetable oils and their derivatives, liquid poly-iso-butylenes (PIB), liquid esters like phthalates, benzoates, sebacates and the like. In those embodiments in which it is judged opportune to add small quantities of said traditional liquid plasticizers, for whatever reasons, e.g. for further prolonging the Open Time of the adhesive, the hot-melt adhesive formulations of the present invention comprise no more than about 15% by weight, preferably no more than about 10% by weight and more preferably no more than about 8% by weight of a traditional liquid plasticizers for hot-melt adhesives (or of a blend of traditional liquid plasticizers) having low molecular weight and a viscosity that is not greater than about 10,000 mPa·s at 50° C., said traditional liquid plasticizer or blend of plasticizers being selected among the above mentioned families of traditional liquid plasticizers. In such a case, mineral oils, both paraffinic, naphthenic and their mixtures are the preferred ones.

Waxes

Again for the above discussed reasons, the hot-melt adhesive formulations according the present invention do not comprise waxes or comprise very low levels of them. This because, as already said, high levels of waxes may strongly impair some of most peculiar and desirable qualities of the adhesive formulations of the present invention, not only owing to their very low molecular weight, but also because of their high crystallinity.

It has been however surprisingly discovered that very low quantities of waxes, not greater than about 5% by weight, preferably not greater than about 3% by weight, can help in fine-tuning, in an even better way, the Solidification Rate from the melt of the present adhesives, and in this way can help in getting an optimized balancing between an excellent initial adhesive strength and an optimum initial cohesion. In such a case polyolefinic waxes, i.e. waxes derived from ethylene, propylene, their copolymers, and especially polypropylene waxes, are the preferred ones. In an even more preferred embodiment of the present invention, said polyolefinic waxes, e.g. polypropylene waxes, are further modified with maleic anhydride.

Other Possible Optional Additives

The hot-melt adhesive formulations described herein, can optionally comprise, in small quantities, even a third polyolefin, substantially non-stereospecific, that is derived from mono-olefins from C2 to C6, provided that its Crystallization Enthalpy from the melt, measured at a cooling rate of 1° C./minute, is not greater than about 25 J/g, preferably not greater than about 20 J/g and more preferably not greater than about 15 J/g.

However, for not impairing the desirable properties of the present adhesives, properties that mainly derive from their very low initial crystallinity, this optional third polyolefin that potentially has a level of initial crystallinity higher than the ones of the preferred two polyolefins, that form the main polymer composition comprised herein, is comprised in the disclosed adhesives at a level not greater than about 15% by weight, preferably not greater than about 10% by weight and more preferably not greater than about 5% by weight.

Moreover the hot-melt formulations according to the present invention, may further comprise from about 0.01% by weight and about 10% by weight of at least one stabilizer, like anti-oxidants, UV photo-stabilizers and their blends. They can further comprise up to a maximum content of about 10% by weight of other optional additives like mineral fillers, pigments, dyes, perfumes, surfactants, antistatic agents.

Detailed Description of Test Methods Used for Measuring Various Parameters

What is following below is the detailed description of test methods used for measuring the main chemical-physical and functional parameters of the hot-melt adhesive formulations of the present invention, and/or of their constituents.

Viscosity

The Brookfield Viscosity as a function of temperature is measured according to the test method ASTM D3236-88.

The shear viscosity at very high shear rate—that, as already mentioned, is a meaningful indicator for a good processability even in processes on high-speed lines—is measured at a typical average processing temperature for hot-melt adhesives, fixed in this case at 160° C., and at a shear rate equal to 100,000 $(s)^{-1}$, by using a Capillary Rheometer type CEAST SR20, supplied by CEAST Instron (Italy).

Melt Flow Rate (MFR)

The Melt Flow Rate (MFR) of a polymer or of a polymer composition is herein measured at 190° C., under a load of 2.16 kg, according to the test method ISO 1133.

Ring & Ball Softening Point (Temperature)

The Ring & Ball Softening Point (Temperature) of the hot-melt adhesives according to the present invention and of their constituents, is measured according to the test method ASTM D36-95. Because the test is performed within 30 minutes after the pouring from the melt into the metallic rings of the material under test, the Ring & Ball Softening Points reported herein have to be considered as values at "time zero".

Volatile Organic Compound (VOC) Value

The content of Volatile Organic Compounds (VOC) in the raw materials, e.g. in tackifiers, and in the formulations according to the present invention, are determined according to the standard test method VDA 278 of the Association of the German Automotive Industry (VDA). In general terms, this measure consists in determining the loss in weight, in a Thermogravimetric Analyzer (TGA) of the sample under test, upon heating at 90° C. for 30 minutes under a stream of Nitrogen.

Needle Penetration

The Needle Penetration of the adhesive formulations disclosed herein, is measured at 55° C., according to the test method ASTM D1321-04. Because the test is performed within at least 120 minutes after the solidification from the melt of the material under test, the Needle Penetrations reported herein have to be considered as values at "time zero".

Open Time

The Open Time of the adhesive formulations under test is measured according to the test method ASTM D4497-94, with the following conditions:

Coating temperature of the adhesive film: 170° C.
Thickness of the adhesive film: 1 mm Peel Strength In the Science of Adhesives, the Adhesive Peel Strength is defined as the average strength per unit of width needed to separate two substrates, bonded by the adhesive under test, measured through a separation test made at a controlled and constant speed, and under a controlled and constant debonding angle. Because the adhesive strength experienced by the final user of the articles in which the present adhesives are used, is the adhesive strength after weeks or months from the manufacturing of the article, herein the adhesive Peel Strength is measured in "aged conditions", i.e. according to the test method ASTM D1876-01, on samples that have been aged and conditioned for seven days at 23° C. and 50% relative humidity.

The substrates of the samples are separated under a debonding angle of 180 degrees, by applying a separation speed of the two substrates equal to 150 mm/minute, that means that the testing dynamometer is actually moving at a speed of 300 mm/minute.

Crystallization Enthalpy at Time Zero or Level of Crystallinity at Time Zero

The measurement, by DSC (Differential Scanning calorimetry) of the Crystallization Enthalpy at Time Zero of the hot-melt adhesive formulations according to the present invention, is, as already highlighted, an especially important parameter because it is at the heart of some of the most peculiar and beneficial properties and behaviors of the present adhesive formulations Because said Enthalpy influences very strongly the formation of the adhesive bond and its initial strength, this measurement is performed by the test method ASTM D3417-99, but slightly modified so to mimic as much as possible in a precise way what happens in reality, during the creation of the adhesive bond itself, starting from the moment when the molten hot-melt adhesive is coated onto the substrate and, through its spontaneous slow cooling and solidification, by natural heat-dispersion and slow decrease in temperature, it forms the adhesive bond with the substrate.

More specifically, to mimic in the best way this spontaneous slow cooling and the solidification of the adhesive on the substrate, the variation rate of the temperature during all the cycles performed according to ASTM D3417-99, has been decreased to 1° C./minute. The above mentioned reasoning is of course primarily important for the first cooling from the melt temperature to −70° C. (see below for more details) during which the initial Crystallization Enthalpy is measured. However, for uniformity of the test method and for comparability of results (e.g. between Crystallization Enthalpies, measured in cooling, and Melting Enthalpies of the formed crystallinities, measured in heating), all the thermal DSC cycles disclosed herein are made at a constant temperature variation rate of 1° C./minute.

More in detail, to measure the Crystallinity at Time Zero of a material, as expressed by the integration of the areas of all the exothermic peaks of crystallization that can be detected by DSC, three consecutive cycles are performed, following under all aspects the procedures of the above mentioned ASTM test method, apart from the variation rate of the temperature, that is kept equal to 1°/minute both in cooling and in heating:

1) The material under test is heated at 1° C./minute, from room temperature to 180° C., in order to mimic the melting process that the hot-melt adhesive undergoes, before being utilized.

2) The molten material is kept at 180° C. for 5 minutes, for equilibrating it.

3) The molten material is cooled, always at the same decreasing rate of temperature equal to 1° C./minute, so to mimic at the best the real phenomena occurring during the real application, slow cooling and solidification of the adhesive with the consequent formation of the adhesive bond. This cooling continues even below room temperature, up to −70° C., so to be able to detect also (just for completeness of information) the Glass Transition Temperature Tg of the material under test.

The integration area of the exothermic crystallization peak or peaks, detected in this experimental phase in temperature decrease, that as well known corresponds to the Crystallization Enthalpy at Time Zero of the tested material, is taken as a measurement of the initial level of crystallinity that said material is able to create.

4) The material is kept again at −70° C. for 5 minutes in order to equilibrate it. 5) The material is heated, again at the temperature variation rate of 1° C./minute, from −70° C. to +180° C. This latest measurement in heating from −70° C. to +180° C., is performed in order to check if there are (as for example, it happens in the adhesive formulation of the following Comparative Example 7) crystallization phenomena at Time Zero that, only due to a kinetic factor, do not appear during the first cycle in decreasing temperature but appear in the consecutive second cycle in increasing temperature (from below Tg up to above melting). In case that part of the initial crystallization occur, for kinetic reasons, also during the second heating cycle, its indicating peaks are thermally positioned between the material's Tg and the following endothermic melting peak or peaks of said overall crystallinity at time zero of the material under test. Therefore, if (as just said, for the following Comparative Example 7) is/are detected, in this second heating phase from −70° C. to +180° C., one or more exothermic crystallization peak or peaks delayed in time, the total crystallinity at Time Zero of the material under test, is considered expressed by the sum of all the exothermic crystallization peaks, detected in the global DSC cycle, both in cooling and in heating.

During all these cycles, the DSC machine records all the phenomena that the material undergoes when somehow changing its state (Tg, melting, crystallizations etc.) and it calculates the relative intensity. In particular, the Crystallization Enthalpy is expressed in J/g and is given by the integration area of the detected exothermic peaks, and their sum is taken as a measure of the overall crystallinity of the material at Time Zero.

Melting Enthalpy After Aging or Level of Crystallinity After Aging

As already mentioned, it has been surprisingly discovered that the hot-melt adhesive formulations according to the present invention, by aging on longer times, undergo a significant variation of some of their properties or of their main physical or chemical parameters, in particular of their level of crystallinity and of their main rheological parameters Elastic Modulus G' and Tan Delta As already said, it has been observed that the final stable asymptotic values for these parameters/properties that significantly change with time, are reached in times that can vary between three and ten days, typically on average in about seven days.

Therefore, for comparing the increase in crystallinity, after aging in time, the aged materials are prepared and tested by DSC in the following way:

1) The material is heated and molten, by heating, from room temperature to 180° C., at the heating rate of 1° C./minute.

2) The molten material is equilibrated by keeping it at 180° C. for 5 minutes.

3) The sample is cooled, at 1° C./minute, from 180° C. to −70° C.

4) It is again equilibrated by keeping it at −70° C. for five minutes.

5) The material is heated from −70° C. to 23° C. at a heating rate of 1° C.

6) At this point, the sample is aged by keeping it, inside the DSC crucible, for seven days at 23° C. and 50% relative humidity.

7) After said aging, the aged material is heated and molten, by heating it at 1° C./minute, from 23° C. to 180° C.

The area of the endothermic peak or peaks of crystalline melting that are observed during step 7), i.e. during the heating of the aged sample from room temperature to 180° C., or, said also in equivalent words, the Melting Enthalpy observed during step 7), are taken as the measure of the overall crystallinity that is present in the tested material after aging.

Solidification Rate as a Function of Temperature at Time Zero

The Solidification Rate from the molten state, around the Rheological Setting Point (called also "Crossing Temperature of the Rheological Moduli", being these two expressions equivalent by definition) is measured in Pa/° C. according to the following method.

As well known to all persons who are averagely expert in the Science of Rheology, in a rheological diagram that shows, as a function of temperature, the main rheological parameters, i.e. the Viscous Modulus G", the Elastic Modulus G' and their ratio Tan Delta, the temperature (in the field of temperatures above room temperature) at which the two moduli cross and where therefore Tan Delta is equal to 1, is taken as the temperature at which the material under test "rheologically solidifies" from the molten state (if said diagram is measured in decreasing temperature) or "rheologically melts" (if the diagram is measured in increasing temperature).

It is also well known that the parameter Elastic Modulus G' represents the "purely solid" character, or also the "hardness", of all physical substances; while the Viscous Modulus G" represents the "purely liquid/fluid" character of all physical substances.

Therefore, if a rheological diagram of a hot-melt adhesive as a function of temperature is measured in decreasing temperature and with a sufficiently slow decreasing rate (in the present case, 2° C./minute), said diagram very well represents the values of the rheological parameters of the adhesive during its application from the molten state on a substrate and its consequent spontaneous slow cooling and solidification during which the adhesive bond is formed.

In particular, by measuring the values of the curve that represents the Elastic Modulus G', in a reasonably limited range of temperatures around the rheological setting point (for example, between +5° C. and −5° C. above and below said point) it is possible to get a significant measurement of the speed by which the adhesive sets and hardens during its spontaneous cooling around its setting point, and during the formation of the adhesive bond with the substrate. Adhesives that "solidify& harden" in a slower way during their cooling and solidification, obviously show a slower increase of G' as a function of decreasing temperature, and they are able to give stronger initial adhesive bonds because they remain softer and tackier for a longer time, even a bit below their setting point.

More in details, the Solidification Rate around the Rheological Setting Point, is measured by the following method: a sample of the material under test is put between the two plates of a rheometer, type Ares-G2, supplied by TA Instruments, and it is heated up to 180° C., where it is completely molten. Then it is equilibrated at this temperature for 30 minutes. At this point the rheological test is started with the recording and measurement, as a function of decreasing temperature of all the rheological parameters, by operating at the frequency of 1 Hz and at the cooling rate of 2° C./minute.

The complete rheological diagram of Temperature Sweep in cooling is measured between the temperatures of +180° C. and −20° C.

In this diagram, after having identified the temperature corresponding to the Rheological Setting Point (as previously defined), are selected all the recorded values of G' comprised between the temperatures positioned 5° C. above and 5° C. below said Setting Point. This group of numerical data is interpolated with a polynomial curve of "n" degree. Said "n" degree of the curve is incremented until its Determination Coefficient $R^2$, that describes the correlation accuracy between the experimental data and the interpolating curve has a value of at least equal to 0.998 (as known an $R^2$ value equal to 1 means an ideal perfect correlation).For information, values of $R^2$ equal to 0.998 or even much higher (for example in some cases even 0.99999) have been obtained in the below described experiments, generally by interpolating the experimental data with a third degree polynomial curve.

After having determined the equation of said curve that accurately interpolates the experimental data, it is calculated, exactly in correspondence with the temperature of the Rheological Setting Point, the mathematical derivative, i.e. by definition the tangent in that point to that curve. As well known, said tangent to the curve expresses the slope of the curve in that point, and therefore the speed at which, at the solidification temperature, G' increases with the decreasing temperature, i.e. how quickly the adhesive solidifies. Said tangent—that has an algebraically negative value because G' increases while the temperature decreases—expresses the value of the Solidification Rate from the molten state around the Rheological Setting Point, $\Delta$ G'/α ° C., therefore expressed in Pa/° C.

Decreasing Rate of Tan Delta as a Function of Temperature at Time Zero

In a fully analogous way, it is possible to measure the initial Decreasing Rate from the molten state of the parameter Tan Delta around the Rheological Setting Point, said parameter being expressed in $°C.^{-1}$ (inverse Celsius degrees) because the parameter Tan Delta is a dimensionless pure number. Also in this case, in the same above described experiment of rheological Temperature Sweep in cooling, it is possible to calculate the equation of the polynomial curve that best interpolates the experimental values of Tan Delta, that are positioned 5° C. above and 5° C. below the Rheological Setting Point.

Once that said equation, that interpolates the experimental data with an accuracy corresponding to a Determination Coefficient $R^2$ equal at least to 0.998, is obtained, it is possible to calculate its tangent (i.e. its slope) exactly in correspondence with the solidification temperature. As already described above, said value of slope, herein expressed in $°C.^{-1}$ (inverse Celsius degrees), expresses the speed by which, at the moment of the solidification and formation of the adhesive bond, the parameter Tan Delta of the adhesive (Tan Delta that expresses, as known, its capability of "flowing & wetting") decreases during the adhesive's cooling.

Lower values of such tangent slope and therefore lower values of the decrement of Tan Delta as a function of the decreasing temperature, well express the capability of a certain adhesive of continuing to flow for a certain time even below its solidification temperature, therefore forming stronger adhesive bond, due both to "chemical" adhesion as well as to mechanical entanglements, formed between the adhesive and the substrate.

Rheological Parameters Elastic Modulus G' and Tan Delta at 23° C. and 1 Hz, at Initial and Aged Conditions Obviously these two rheological parameters at room temperature and their variations with aging in time are measured on the solid materials according to the test method ASTM D5279-13, i.e. by testing them in torsion and in the form of rectangular bars, on a rheometer type Ares-G2, supplied by TA Instruments.

Said bars are poured from the melt at 170° C. into a PTFE mold and allowed to solidify and cool to room temperature. They have a width of 12 mm, a thickness of 6 mm and the jaw separation distance on the testing rheometer is equal to 10 mm.

In its original form, the above mentioned ASTM test method D5279-13 recommends a conditioning of the rectangular test specimens for not less than 40 hours at 23° C. and 50% Relative Humidity.

However, because in our case, the scope is to compare the variation with time of the rheological parameters Elastic Modulus G' and Tan Delta, between initial and aged conditions, said recommendation of the ASTM method is modified in the following way.

Values of G' and Tan Delta at Time Zero are measured in torsion at the frequency of 1 Hz with rectangular specimens at about 60 minutes after their solidification into the mold, and in any case at a time not longer than 120 minutes from their solidification.

Values of G' and Tan Delta in aged conditions are measured in torsion at the frequency of 1 Hz with rectangular specimens that, after their pouring and solidification into the mold, are left to age for seven days at 23° C. and 50% Relative Humidity.

Rheological Parameter Aged Elastic Modulus G' at 37° C. at the Frequency of 0.01 Hz As already explained, a sufficiently high value of this Aged Elastic Modulus G' at 37° C. at the frequency of 0.01 Hz is important for assuring an adequate resistance in use of the hot-melt adhesive formulations according to the present invention, when they are applied into hygienic absorbent articles, during their use on the body of the wearer.

This parameter is measured in torsion, on aged rectangular specimens, in a fully similar way like specified in the previous paragraph for aged values of G'.

Of course, the difference in test conditions versus the previous paragraph is that the rheological test in torsion is done at 37° C. and under a frequency of 0.01 Hz.

Assessment of the Processability at High Speed and of the Aged Adhesive Strength of the Adhesive Formulations The adhesive strength of the hot-melt adhesive formulations considered herein has been evaluated by measuring the aged adhesive property known in the field as Peel Strength, i.e. the average strength per unit of width needed to separate two substrates, bonded by the adhesive formulation under test, said strength being measured through a separation made at constant speed and under a constant debonding angle.

More in details said Peel Strength has been measured according to the method ASTM D1876-01, therefore under a constant debonding angle of 180 degrees and by applying a separation speed between the two bonded substrates equal to 150 mm/minute, therefore at a moving speed of the used dynamometer equal to 300 mm/minute.

As already highlighted, because the adhesive strength experienced by the final user of the articles in which the present adhesives are used, is the adhesive strength after weeks or months from the manufacturing of the article, herein the adhesive Peel Strength is measured in "aged conditions", on samples that, after their preparation, have been aged and conditioned for seven days at 23° C. and 50% relative humidity.

More in details, the samples to be tested for their adhesive peel strength have been manufactured in the following way: the hot-melt adhesive formulations under test have been extruded at the temperature of 175° C. on a pilot line that mimics an industrial line for the manufacturing of absorbent hygienic articles, like diapers for infants and toddlers.

The pilot line has been utilized at the line speed of 300 m/minute that is representative of the very high line speeds at which are really operated the actual industrial lines for the manufacturing of said absorbent hygienic articles.

Each adhesive under test has been extruded through a flat extrusion-die on a polyethylene film having a basis-weight of 22 $g/m^2$, supplied by Poligof (Italy). The extrusion has been made by coating the adhesive on the film, in the shape of multiple parallel lines, each line having a basis-weight of coated adhesive equal to 15.4 $g/m^2$. Each line of adhesive is 1 mm wide and the distance between two lines of adhesive, contiguous and parallel, is equal to 1 mm.

The molten adhesive is coated on the plastic film and this film is immediately contacted and joined, without applying any compression and pressure, with a perforated polyethylene film, supplied by Plastik (Italy) with the trade mark Drytex, having multiple holes, with a conical shape, of about 0.8 to 1 mm of maximum opening and separated by unperforated spaces that are on average about 0.4-0.5 mm wide.

Once that the bonding between the two polyethylene substrates has been formed, the bonded structure is cut, in a cross-direction referred to the adhesive lines, in strips having a width of 1 inch (25.4 mm). The samples are conditioned for seven days at 23° C. and 50% relative humidity, as also recommended by the ASTM method, and then tested in the adhesive Peel Test.

The measurement of the Peel Strength is performed, according to the above mentioned ASTM test method, by debonding a bonded strip in a cross-direction referred to the lines of adhesive. Because the sample contains lines that are glued by the adhesive alternated to lines in which no adhesive is present, the measured adhesive strength is calculated as the average value of the various peaks of strength that are detected in correspondence with each bonded line. For each tested adhesive formulation, ten specimens are tested, and the final adhesive Peel Strength result—reported for the various adhesives in the following Table 1—is the average value of the single ten specimens.

For applications in the field of absorbent hygienic articles, the Peel Strength required for a perforated plastic film is typically not lower than about 0.5 N/inch (0.197 N/cm), preferably not lower than about 0.8 N/inch (0.315 N/cm) and more preferably not lower than about 1.0 N/inch (0.394 N/cm).

The present invention is better illustrated by the following examples, which are given merely for the purpose of illustration and are not to be regarded as limiting the scope of the invention or the manner in which it can be practiced. Unless specifically indicated otherwise, parts and percentages are given by weight.

Examples According to the Invention

EXAMPLE 1

The following hot-melt adhesive formulation, according to the present invention, has been prepared by mixing its constituents in the molten state at 170° C.:

| Ingredient | % by weight on the total weight of the adhesive formulation | Nature and supplier |
| --- | --- | --- |
| Rextac 2715 | 45.5 | Non-stereospecific Polyolefinic Copolymer supplied by Rextac (USA) |
| Rextac 2730 | 45.5 | Non-stereospecific Polyolefinic Copolymer supplied by Rextac (USA) |
| Licocene PPA 330 | 6.0 | C3-C2 metallocenic polyolefinic copolymer, highly non-stereospecific and non-solid at room temperature, supplied by Clariant (Switzerland) |
| AC-596 | 2.0 | Polypropylenic wax modified with maleic anhydride, supplied by Honeywell (USA) |
| Irganox 1010 | 1.0 | Antioxidant supplied by BASF (Germany) |

The hot-melt adhesive formulation of Example 1 according to the present invention, comprises, as its main polymeric constituent and for as much as 91% by weight, a polymer composition formed, in equal quantities, by two polyolefinic copolymers, non-stereospecific and having a low individual crystallinity, both of them being mainly composed of propylene and having a very similar overall chemical composition.

More precisely both Rextac 2730 and Rextac 2715 are believed to be copolymers (more precisely terpolymers) containing about 67.5 by mole propylene, about 30.5% by mole butene-1 and about 2% by mole ethylene.

It is believed that Rextac 2730 has an average Number Molecular Weight Mn equal to about 8,330 g/mole, an average Mass Molecular Weight Mw equal to about 59,100 g/mole and a viscosity at 190° C. equal to about 3,000 mPa·s; while Rextac 2715 is believed to have an average Number Molecular Weight Mn equal to about 6,600 g/mole, an average Mass Molecular Weight equal to about 51,200 g/mole and a viscosity at 190° C. equal to about 1,500 mPa·s.

Therefore, in said polymer composition that forms the 91% by weight of the hot-melt adhesive formulation showed in Example 1, the two constituting non-stereospecific polyolefins have a difference between their single average Number Molecular Weights Mn as small as about 1,700 g/mole and a difference between their single average Mass Molecular Weights Mw equal to about 7,900 g/mole.

When tested at time zero according to the previously described DSC cycles, said polyolefinic copolymers have low individual initial crystallinities, as expressed by the low values of their Crystallization Enthalpies at time zero, measured, as said, at the temperature decreasing rate of 1° C./minute. In said conditions, Rextac 2730 shows a Crystallization Enthalpy at time zero of about 8.0 J/g with one crystallization peak centered at about 65.8° C.; while Rextac 2715 shows an initial Crystallization Enthalpy as low as 3.1 J/g, with one peak of crystallization centered at about 73.8° C.

The hot-melt adhesive formulation of Example 1 does not comprise either tackifiers and traditional liquid plasticizers at low molecular weight, like for example mineral oils or poly-iso-butylene oils (PIB).

It contains a small quantity of a polymeric viscosity modifier, that is highly non-stereospecific and that is non-solid at room temperature, traded with the trade mark Licocene PPA 330 by Clariant. It is a metallocenic polyolefinic copolymer, highly non-stereospecific and non-solid at room temperature, that is believed to be a copolymer of propylene with a minor quantity of ethylene.

At room temperature this polymer appears as a gelatinous transparent and colorless mass with such a high viscosity that it is practically non-measurable e.g. with the test method ASTM D3236-88. However at room conditions, this polymer is certainly "non-solid"—according to the definition previously given for this term—because this gelatinous polymer, in spite of the fact that it is sufficiently highly viscous to be temporarily shaped per se into whatever tridimensional form, once that it is left at rest, without any external stress or strength, apart from its own weight, slowly permanently deforms and spontaneously flows, so that it loses, after less than about one hour, its own initial form, and assumes the shape of the container in which it is contained or of the plane on which it is resting.

This very high viscosity at room temperature helps the cohesion of the formulation of Example 1 in its conditions of use at low temperatures. However Licocene PPA 330 decreases unexpectedly quickly its viscosity with an increase in temperature over room temperature. For example at 50° C. it has a still high viscosity, but that is now measurable and equal to about 16,300 mPa·s; and already at 100° C. its viscosity is as low as 1,050 mPa·s and at 190° C. is as low as just 98 mPa·s.

This very high fluidity at high temperatures helps a low viscosity and an optimum processability in the hot-melt adhesives in which Licocene PPA 330 is included as an additive, without impairing, as already said, also an optimum cohesion, since Time Zero, at room temperature.

Moreover Licocene PPA 330 does not introduce into the final adhesive formulation any crystallinity because its non-stereospecificity seems practically total. In fact, if tested in the test for measuring the initial Crystallization Enthalpy, Licocene PPA 330 does not show any initial crystallization peak and therefore its initial Crystallization Enthalpy is to be considered practically equal to zero.

The adhesive formulation of Example 1 comprises only a very small quantity, i.e. 2% by weight, of a low molecular weight compound that has a not negligible crystallinity, i.e. the wax AC 596 that is a polypropylenic wax modified with small quantities of maleic anhydride. In such small quantities said wax is useful not only for tuning in an optimum way the solidification rate from the melt of the present adhesives, through the very small quantity of initial crystallinity added to the formulation in this way, but also, through the well known effect of maleic anhydride in hot-melt adhesives, concurs to further increase the initial adhesive strength.

In any case, the adhesive formulations of Example 1 possesses a surprisingly low initial crystallinity, as expressed by its Crystallization Enthalpy at Time Zero that is equal to as low as 4.0 J/g, and therefore even by about 28% lower that the weighted average value of the single Crystallization Enthalpies of the two non-stereospecific polyolefins that form the polymer composition comprised in such a formulation at a level of 91% by weight.

This fact demonstrates that the blending, in opportune ratios, of the two non-stereospecific polyolefins inside the polymer composition, leads to a further and significant decrease of the overall initial crystallinity, at time zero, with all the consequent beneficial effects, compared to the option of using only one polyolefin.

In spite of the absence of traditional liquid plasticizers and of tackifiers at low molecular weight, the adhesive formulation of Example 1 shows a rather low melt viscosity, equal to 4,540 mPa·s at 150° C. and to 2,630 mPa·s at 170 C.

Moreover it has a Ring & Ball softening point of 115.5° C.; a Needle Penetration at 55° C. equal to 105 dmm; a slow Solidification Rate around its Rheological Setting Point (that is equal to 63.6° C.) that is −1,455 Pa/° C.; a slow Decreasing Rate of Tan Delta, still around its Rheological Setting Point, that is 0.047 (° C.)$^{-1}$; a sufficiently long Open Time equal to about 3 minutes and 30 seconds.

The adhesive formulation of Example 1 is able also to increase in a substantial way with aging both its adhesive strength and cohesion. This is shown by the significant increase, after aging for seven days at 23° C. and 50% Relative Humidity, of its crystalline content (Table 2), of its Elastic Modulus G', measured at 23° C. and 1 Hz (Table 3) and by the decrease of its rheological parameter Tan Delta at 23° C. and 1 Hz (Table 4). More precisely its Crystalline Enthalpy after aging is equal to 7.2 J/g with an increase of 80% over its initial crystallization Enthalpy of 4.0 J/g; its aged Elastic Modulus G' at 23° C. has a value of 2.593 MPa i.e. 101.8% higher than its initial G' equal to 1.285; and the Tan Delta at Time Zero and 23° C., that is equal to 0.45, after aging decreases to 0.24 with a percent decrement of −46.7%.

The present hot-melt adhesive formulation shows also an aged Elastic Modulus G', measured at 37° C. and at the frequency of 0.01 Hz, equal to 443,500 Pa, that assures an adequate resistance in use when this adhesive is applied into hygienic absorbent articles, during their use on the body of the wearer.

The adhesive formulation of Example 1 shows an optimum processability even in processes at very high linespeed, and it shows a high initial adhesion even on substrates that are particularly difficult to be bonded like perforated plastic films, as it is demonstrated by the experimental results of aged adhesive Peel Strength on a pilot line running at 300 m/minute, as illustrated below (see Table 1). The excellent processability of this formulation at high linespeed is also meaningfully expressed by its low shear viscosity at high shear. In fact e.g. at 160° C. and at a shear rate of 100,000 (s), the adhesive formulation of Example 1 shows a shear viscosity as low as 420 mPa·s.

EXAMPLE 2

The following hot-melt adhesive formulation, according to the present invention, has been prepared by mixing its constituents in the molten state at 170° C.:

| Ingredient | % by weight on the total weight of the adhesive formulation | Nature and supplier |
|---|---|---|
| Rextac 2715 | 15.0 | Non-stereospecific Polyolefinic Copolymer supplied by Rextac (USA) |
| Rextac 2730 | 71.0 | Non-stereospecific Polyolefinic Copolymer supplied by Rextac (USA) |
| Licocene PPA 330 | 6.0 | C3-C2 metallocenic polyolefinic copolymer, highly non-stereospecific and non-solid at room temperature, supplied by Clariant (Switzerland) |
| AC-596 | 2.0 | Polypropylenic wax modified with maleic anhydride, supplied by Honeywell (USA) |
| Primol 352 | 5.0 | Paraffinic mineral oil supplied by ExxonMobil |
| Irganox 1010 | 1.0 | Antioxidant supplied by BASF (Germany) |

The hot-melt adhesive formulation of Example 2 is similar to the formulation of Example 1, especially because it does not comprises any tackifier and because its main polymer constituent, present for as much as 86% by weight, is a polymer composition formed by the two non-stereospecific polyolefinic copolymers Rextac 2730 and Rextac 2715. Also most of the other minor constituents are equal to Example 1 and are present at the same low quantities.

The only difference, besides a different ratio in weight between the two non-stereospecific polyolefins, is the addition of a small quantity, just 5% by weight, of a liquid plasticizer, i.e. of a paraffinic mineral oil, that is particularly compatible with the base polyolefin composition.

Also the adhesive formulation of Example 2 shows an initial residual crystallinity that is surprisingly low, as expressed by its Crystallization Enthalpy at time zero that is equal to as low as 4.3 J/g, therefore even lower for about 40% than the weighted average value of the single Crystallization Enthalpies of the two non-stereospecific polyolefins constituting the polymer composition contained for about the 86% of its weight.

The adhesive formulation of Example 2 has a viscosity of 4,460 mPa·s at 150° C. and of 2,550 mPa·s at 170° C.; it has also a Ring & Ball Softening Point of 114.7° C.; a Needle Penetration at 55° C. equal to 113 dmm; a Solidification Rate around its Rheological Solidification Point (that is equal to 61.6° C.) that is −1,520 Pa/° C.; a Decreasing Rate of Tan Delta, still around its Rheological Solidification Point, that is 0.063 (° C.)$^{-1}$; an Open Time equal to 3 minutes.

Also the adhesive formulation of Example 2 is able to significantly vary its crystallinity and its rheological parameter over aging, with a consequent beneficial increase both in adhesive strength and cohesion. More specifically, the low initial Crystallization Enthalpy of 4.3 J/g, after seven days of aging at 23° C. and 50% relative humidity, increases to a crystalline Enthalpy of 8.8 J/g with a percent increase of 104.7%. A similar behavior is observed for rheological parameters at room temperature: for example the Elastic Modulus G' at 23° C. and 1 Hz from an initial value of 1.165 MPa, after aging equals 2.289 MPa with an increase of 96.5%; while Tan Delta at 23° C. and 1 Hz, that at Time Zero has a value of 0.472, after aging, decreases to 0.275, with a decrement of −41.7%.

The hot-melt adhesive formulation of Example 2 shows also an aged Elastic Modulus G', measured at 37° C. and at the frequency of 0.01 Hz, equal to 347,800 Pa, that assures an adequate resistance in use when this adhesive is applied into hygienic absorbent articles, during their use on the body of the wearer.

As for the previous formulation of Example 1, also the above formulation has an optimum processability even at a line speed as high as 300 m/minute and shows an excellent initial adhesive strength even on difficult to bond substrates like a perforated film.

EXAMPLE 3

The following hot-melt adhesive formulation, according to the present invention, has been prepared by mixing its constituents in the molten state at 170° C.:

| Ingredient | % by weight on the total weight of the adhesive formulation | Nature and supplier |
| --- | --- | --- |
| Rextac 2715 | 45.5 | Non-stereospecific Polyolefinic Copolymer supplied by Rextac (USA) |
| Rextac 2730 | 45.5 | Non-stereospecific Polyolefinic Copolymer supplied by Rextac (USA) |
| Licocene PPA 330 | 3.0 | C3-C2 metallocenic polyolefinic copolymer, highly non-stereospecific and non-solid at room temperature, supplied by Clariant (Switzerland) |
| AC-596 | 2.0 | Polypropylenic wax modified with maleic anhydride, supplied by Honeywell (USA) |
| Sukorez NX-710 | 3.0 | Tackifier supplied by Kolon (South Korea) |
| Irganox 1010 | 1.0 | Antioxidant supplied by BASF (Germany) |

The adhesive formulations of Example 3 is very similar to the previous Example 1, apart from the addition of a minimal quantity, as low as just 3% by weight, of a tackifier Sukorez NX-710, supplied by Kolon (South Korea) and that is a hydrogenated tackifier with a softening point equal to about 110° C.

Like for Example 1, also the adhesive formulation of Example 3 possesses a surprisingly low initial crystallinity, as expressed by its Crystallization Enthalpy at Time Zero that is equal to as low as 3.6 J/g, and therefore even by about 35% lower that the weighted average value of the single Crystallization Enthalpies of the two non-stereospecific polyolefins that form the polymer composition comprised in Example 3 at a level of 91% by weight.

The adhesive formulation of Example 3 has a melt viscosity of 4,840 mPa·s at 150° C. and of 2,750 mPa·s at 170° C.; it has also a Ring & Ball Softening Point of 115.3° C.; a Needle Penetration at 55° C. equal to 95 dmm; a Solidification Rate around its Rheological Solidification Point (equal to 62.6° C.) that is −1,833 Pa/° C.; a Decreasing Rate of Tan Delta, still around its Rheological Solidification Point, that is 0.048 (° C.)$^{-1}$ a sufficiently long Open Time equal to about 3 minutes and 30 seconds.

Also this adhesive formulation according to the present invention shows, besides the above mentioned optimum general parameters, also a significant controlled "hardening" with aging, as highlighted by the increase in crystalline content and by the variations of its rheological parameters Elastic Modulus G' and Tan Delta at room conditions. More precisely, the very low initial crystallization Enthalpy of 3.6 J/g, after the usual seven days of aging at room conditions, shows a substantially higher crystallinity as expressed by an aged Crystalline Enthalpy of 6.3 J/g with a percent increase of 75%; the rheological parameter Elastic Modulus G' at 23° C. and 1 Hz passes from a value of 1.244 MPa at Time Zero to an aged value of 2.492 MPa with a percent increase of 100.3%; Tan Delta at 23° C. and 1 Hz that initially has a value of 0.457, after seven days of aging, is equal to 0.253 with a decrement of −44.6%.

Also for the hot-melt adhesive formulation of Example it is possible to measure an aged Elastic Modulus G', at 37° C. and at the frequency of 0.01 Hz, equal to 300,800 Pa, that assures an adequate resistance in use when this adhesive is applied into hygienic absorbent articles, during their use on the body of the wearer.

As for the previous two formulations, also the adhesive of Example 3 has an optimum processability even at a line speed as high as 300 m/minute and shows an excellent initial adhesive strength even on difficult to bond substrates like a perforated film.

EXAMPLE 4

The following hot-melt adhesive formulation, according to the present invention, has been prepared by mixing its constituents in the molten state at 170° C.:

| Ingredient | % by weight on the total weight of the adhesive formulation | Nature and supplier |
| --- | --- | --- |
| Rextac 2715 | 43.5 | Non-stereospecific Polyolefinic Copolymer supplied by Rextac (USA) |
| Rextac 2730 | 43.5 | Non-stereospecific Polyolefinic Copolymer supplied by Rextac (USA) |
| Licocene PPA 330 | 3.0 | C3-C2 metallocenic polyolefinic copolymer, highly non-stereospecific and non-solid at room temperature, supplied by Clariant (Switzerland) |
| AC-596 | 2.0 | Polypropylenic wax modified with maleic anhydride, supplied by Honeywell (USA) |
| Sukorez NX-710 | 7.0 | Tackifier supplied by Kolon (South Korea) |
| Irganox 1010 | 1.0 | Antioxidant supplied by BASF (Germany) |

The adhesive formulation of Example 4 is very similar to the previous Example 3 but it contains a slightly higher level of the hydrogenated hydrocarbon tackifier Sukorez NX-710 for further increasing its tackiness.

Also in this Example 4 the initial crystallinity is surprisingly low, as expressed by its Crystallization Enthalpy at Time Zero that is equal to as low as 3.7 J/g, and therefore it is even by about 33% lower that the weighted average value of the single Crystallization Enthalpies of the two non-stereospecific polyolefins that form the polymer composition comprised in such a formulation at a level of 87% by weight.

This adhesive formulation of Example 4 has a viscosity of 5,000 mPa·s at 150° C. and of 2,780 mPa·s at 170° C.; it has a Ring & Ball Softening Point of 115.7° C.; a Needle Penetration equal to 110 dram; a Solidification Rate around the Rheological Setting Point (that is equal to 61.0° C.) that is −1,870 Pa/° C.; a Decreasing Rate of Tan Delta, still around the Rheological Setting Point, that is 0.043 (° C.)$^{-1}$; an Open Time equal to 4 minutes and 30 minutes.

Also the adhesive formulation of Example 4 shows a significant positive effect of aging on its crystallinity and its rheological parameters at room temperature, that, combined with the above mentioned other optimal parameters, further improve with aging the already excellent initial adhesive strength and cohesion. Its low initial Crystallization Enthalpy of 3.7 J/g, after seven days of aging at room conditions, increases to a Crystalline Enthalpy of 6.5 J/g with an increase of 75.7%; its initial Elastic Modulus G' at 23° C. and 1 Hz, equal to 1.121 MPa, after aging passes to 1.935 MPa with an increase of 72.6%; its Tan Delta at 23° C. and 1 Hz that, at Time Zero, equals 0.477, after aging has a significantly lower value of 0.266 with a percent decrease of −44.2%.

Finally also the hot-melt adhesive formulation of Example 4 has an aged Elastic Modulus G', measured at 37° C. and at the frequency of 0.01 Hz, equal to 293,500 Pa, that assures an adequate resistance in use when this adhesive is applied into hygienic absorbent articles, during their use on the body of the wearer.

As for the three previous formulations, also the above formulation of Example 4 has an optimum processability even at a line speed as high as 300 m/minute and shows an excellent initial adhesive strength even on difficult to bond substrates like a perforated film.

COMPARATIVE EXAMPLES

COMPARATIVE EXAMPLE 1

The following hot-melt adhesive formulation has been prepared by mixing its constituents in the molten state at 170° C. but not observing the teachings and requirements of the present invention:

| Ingredient | % by weight on the total weight of the adhesive formulation | Nature and supplier |
| --- | --- | --- |
| Rextac 2730 | 67.5 | Non-stereospecific Polyolefinic Copolymer supplied by Rextac (USA) |
| Vestoplast 751 | 16.0 | Non-stereospecific Polyolefinic Copolymer supplied by Evonik (Germany) |
| Licocene PPA 330 | 6.0 | C3-C2 metallocenic polyolefinic copolymer, highly non-stereospecific and non-solid at room temperature, supplied by Clariant (Switzerland) |
| AC-596 | 2.0 | Polypropylenic wax modified with maleic anhydride, supplied by Honeywell (USA) |
| Primol 352 | 7.5 | Paraffinic mineral oil supplied by ExxonMobil |
| Irganox 1010 | 1.0 | Antioxidant supplied by BASF (Germania) |

The hot-melt adhesive of Comparative Example 1 is very similar to the previous Example 2 according to the present invention, but it does not respects the requirement that the molecular weights of the two non stereospecific polyolefinic polymers that form the base polymer composition, are not too much different.

In fact, the second non-stereospecific polymer (that substitutes the previous Rextac 2715 of Example 2) is Vestoplast 751, a propylene-ethylene copolymer, with prevailing propylene, supplied by Evonik (Germany). Vestoplast 751 per se is not excessively crystalline having in its pure state an initial crystallization Enthalpy of 12.6 J/g. However it has an excessively high molecular weight (compared to the other present non-stereospecific polyolefin Rextac 2730), as demonstrated also by its melt viscosity that is very high and equal to about 50,000 mPa·s at 190° C. In fact it is believed that Vestoplast 751 has an average Number Molecular Weight Mn equal to about 18,800 g/mole and an average Mass Molecular Weight equal to about 88,000 g/mole.

Therefore, in the polymer composition comprised in the formulation of Comparative Example 1 for 83.5% by weight, the difference between the average Number Molecular Weights of the two forming polyolefins, Mn(A)-Mn(B), is significantly higher than what is requested by the present invention and is equal to 10,500 g/mole; similarly, the difference between the two average Mass Molecular Weights of the same two polyolefins, Mw(A)-Mw(B), is too high and equal to 28,900 g/mole. The melt viscosity of the Comparative Example 1 is significantly higher than the one of the previous Example 2 and is equal to 5,000 mPa·s at 170° C. and to 8,500 mPa·s at 150° C.

Other parameters of the hot-melt adhesive of Comparative Example 1 are on the contrary rather similar to the ones of the previous Example 2, according to the present invention. For example, this adhesive formulation has an initial Crystallization Enthalpy of 4.3 J/g; a Ring & Ball Softening Point of 115.5° C.; a Needle Penetration at 55° C. of 105 dmm; a Solidification Rate around its Rheological Setting Point (that is equal to 60.8° C.) that is −1,475 Pa/° C.; a Decreasing Rate of Tan Delta, again around the Rheological Setting Point, that is 0.04 (° C.)$^{-1}$; an Open Time equal to 2 minutes and 30 seconds.

However, as showed in the following Table 1, the adhesive formulation of the present Comparative Example 1, because it does not fulfills all the requirements of the adhesive formulations according to the present invention, shows a very poor processability on a high speed line. In fact, in the previously described conditions for the bonding of a perforated plastic film at a line speed of 300 m/minute, it has been tried in vain to process and apply this formulation at all the temperatures comprised between 150° C. and 190° C., at intervals of 5° C., (being 190° C. a temperature already unacceptably high for the bonding of polyethylene plastic films) in the vain attempt of finding a temperature that might have allowed a regular extrusion and a sufficiently strong bonding; but it was impossible to find any operative condition that might allow a regular and industrially acceptable processing.

The behavior after aging for seven days at room conditions of the adhesive formulation of Comparative Example 1 somehow follows, under certain aspects, the behavior of the very similar formulation of the previous Example 2, while under other aspects is quite different, most likely due to the "disturbing presence" of the constituent Vestoplast 751 with very high molecular weight that may disturb a sufficiently good "hardening" with aging.

Specifically the adhesive formulation of Comparative Example 1, after aging for seven days at 23° C. and 50% Relative Humidity, shows a lower increase in crystalline content as expressed by a percent increase of crystalline Enthalpy of 53.5%, given by a comparison between an initial Crystalline Enthalpy of 4.3 J/g and an aged Crystalline Enthalpy of 6.6 J/g.

The variations with aging in the rheological parameters of Comparative Example 1 are even more unsatisfactory: in fact the Elastic Modulus G' at 23° C. and 1 Hz that, at Time Zero, has a value of 1.294 MPa, after seven days of aging G' has a value of as just 1.597 with a percent increase of only 23.4%; equally Tan Delta at 23° C. and 1 Hz, that at Time Zero has a value of 0.419, after aging shows a value of 0.342 with a decrement of only −18.4%.

COMPARATIVE EXAMPLE 2

The following hot-melt adhesive formulation has been prepared by mixing its constituents in the molten state at 170° C. but not observing all the teachings and requirements of the present invention and on the contrary following the teachings of a part of the Prior Art:

| Ingredient | % by weight on the total weight of the adhesive formulation | Nature and supplier |
|---|---|---|
| Rextac 2780 | 30.0 | Non-stereospecific Polyolefinic Copolymer supplied by Rextac (USA) |
| Rextac 2304 | 69.5 | Non-stereospecific Polyolefinic Copolymer supplied by Rextac (USA) |
| Irganox 1010 | 0.5 | Antioxidant supplied by BASF (Germany) |

The adhesive formulation of Comparative Example 2 comprises only (apart from a very small quantity of an antioxidant) a polymer composition formed by two non-stereospecific polyolefinic copolymers, that however have not a sufficiently low initial crystallinity, as indicated by their single Crystallization Enthalpies at Time Zero that are both higher than 12 J/g. Rextac 2780 is a non-stereospecific copolymer that has a chemical composition relatively similar to the already previously mentioned Rextac 2730 and Rextac 2715; it contains about 68% by mole of propylene and 32% by mole of butene-1. However it has higher molecular weights, and more precisely an average Number Molecular Weight equal to about 13,700 g/mole and an average Mass Molecular Weight equal to about 80,000 g/mole.

Moreover Rextac 2780 has an initial level of crystallinity that is not sufficiently low being his initial Crystallization Enthalpy equal to 12.5 J/g.

With its high molecular weights and its not negligible initial crystallinity, Rextac 2780 can give a good initial cohesion to an adhesive.

However for not having excessive melt viscosities that would make the adhesive not processable (per se Rextac 2780 has a viscosity of about 8,000 mPa·s at 190° C.), in the polymer composition of the above comparative formulation, Rextac 2780 has been blended with a preponderant quantity of Rextac 2304.

This polymer is a copolymer of propylene and ethylene, that is believed to comprise about 10% by mole ethylene, and that has rather low molecular weights and melt viscosity. In fact Rextac 2304 has a viscosity at 1190° C. as low as 450 mPa·s; its average Number Molecular Weight Mn is about 7,200 g/mole and its average Mass Molecular Weight Mw is about 35,000 g/mole.

Therefore, the differences between the molecular weights of the two non-stereospecific polyolefins that form the polymer composition comprised in the formulation of Comparative Example 2 are excessively large; more specifically, referring to the difference between the average Number Molecular Weights, Mn(A)−Mn(B), it is equal to 6,500 g/mole; while, referring to the difference between the average Mass Molecular Weights, Mw(A)−Mw(B), it is equal to 51,000 g/mole.

Moreover, the initial Crystallization Enthalpy of this formulation is also relatively high, being equal to 12,2 J/g, and indicating therefore a not negligible content of crystallinity at Time Zero.

Furthermore, this adhesive formulation has a melt viscosity of 5,600 mPa·s at 150° C. and of 1,890 mPa·s at 170° C.; it has a high Ring & Ball Softening Point equal to 128,7° C.; a Needle Penetration at 55° C. equal to 90 dmm.

However, given its initial level of crystallinity not sufficiently low, this adhesive has a Solidification Rate around its Rheological Setting Point (that is equal to 88.8° C.) that is too fast and equal to −3,545 Pa/° C.; and even more it shows an excessively high initial Decreasing Rate of Tan Delta, still around the Rheological Setting Point, that is as high as 1.445 (° C.)$^{-1}$.

As a consequence also its Open Time is too short for giving a good processability and is just equal to 1 minute. And in fact, as showed by the following Table 1, the adhesive formulation of the present Comparative Example 2, because it does not fulfill all the requirements pf the hot-melt adhesive formulations according to the present invention, shows an unacceptably low Peel Strength as low as 0.2 N/inch (0.079 N/cm).

As already described, all the above mentioned unsatisfactory parameters of Comparative Example 2, especially e.g. the high initial crystallinity and hardness, the too short Open Time and the too rapid setting rate around the Rheological Setting Point, prevent the formation of good adhesive bonds with sufficiently high adhesive strength since the very first moment when the molten adhesive is put in contact with the substrates (insufficient wetting of the substrate, insufficient contact area with the substrate, too hard and not tacky adhesive); and therefore even a hardening with aging of said adhesive formulation is unable to increase to acceptable levels the adhesive strength, as demonstrated by the very low aged Peel Strength showed in Table 1. Therefore the adhesive formulation of Comparative Example 2, even if it shows with aging a certain increase in crystallinity (anyhow low) and a certain variation in its rheological parameters G' and Tan Delta, is unable anyhow to reach a level of acceptable final adhesive strength, because are lacking those initial conditions of good wetting, large contact area etc. that are indispensable since the very first moment for the creation of good adhesive bonds. In any case, just for the sake of documentation, the adhesive formulation of Comparative Example, that, at Time Zero, has a rather high Crystalline Enthalpy of 12.2 J/g, after aging for seven days at 23° C. and 50% Relative Humidity, shows a Crystalline Enthalpy of 16.1, i.e. increased in percentage of 32%; its Elastic Modulus G', at 23° C. and 1 Hz, at Time Zero, has a value of 1.823 MPa, and after aging is 3.532 MPa, therefore with a percent increase of 93.7%; while the rheological parameter Tan Delta, measured at 23° C. and 1 Hz, at Time Zero is 0.364 and after aging is 0.320 with a percent variation equal to −12.1%.

COMPARATIVE EXAMPLE 3

The below hot-melt adhesive formulation has been prepared by mixing its constituents in the molten state at 170° C. and by following the teachings of a part of the Prior Art:

| Ingredient | % by weight on the total weight of the adhesive formulation | Nature and supplier |
|---|---|---|
| Rextac 2814 | 89.5 | Non-stereospecific Polyolefinic Copolymer supplied by Rextac (USA) |
| Polybond 3200 | 10.0 | Highly crystalline isotactic Polypropylene modified with maleic anhydride, supplied by Addivant (USA). |
| Irganox 1010 | 0.5 | Antioxidant supplied by BASF (Germany) |

In the adhesive formulation of Comparative Example 3, the Prior Art tries to balance initial adhesive strength and cohesion in an adhesive that is based on a non-stereopecific polyolefinic copolymer, by adding 10% by weight of an isotactic polypropylene having a very high crystallinity and a high molecular weight, modified with about 1% by weight of maleic anhydride, traded with the mark Polybond 3200 by Addivant (USA).

The utilized non-stereospecific polyolefinic copolymer is Rextac 2814, that is a copolymer containing about 55% by mole butene-1 and about 45% by mole propylene. Its melt viscosity at 190° C. is about 1,400 mPa·s, and it is believed that its average Number Molecular Weight Mn is about 7,500 g/mole, while its average Mass Molecular Weight Mw is about 52,500 g/mole. The initial residual crystallinity of Rextac 2814 is not at all negligible as indicated by the Crystallization Enthalpy at time zero of this polymer that is equal to 16.9 J/g.

The isotactic crystalline polypropylene Polybond 3200 has an even much greater initial Crystallization Enthalpy and equal to as much as 91.7 J/g; its average Number Molecular weight Mn is about 46,200 g/mole and its average mass Molecular Weight Mw is about 120,000 g/mole.

The hot-melt adhesive formulation of Comparative Example 3 shows two peaks of crystallization in the first cooling DSC cycle, for an overall initial Crystallization Enthalpy at Time Zero equal to 17.3 J/g. Its Rheological Setting point is positioned at the very high temperature of 104.2° C.; around this point, its Solidification Rate is of −2,130 Pa/° C., and its Decreasing Rate of Tan Delta is as high as 1.04 (° C.)$^{-1}$.

Its Ring & Ball Softening Point is also very high and equal to as much as 152.2° C. that makes this formulation not processable in the conditions that are requested for the bonding of plastic films in absorbent hygienic articles; the same is valid for its too high viscosity that is equal to as much as 23,000 mPa·s at 150° C.

Like for the adhesive formulation of Comparative Example 1, also for the formulation of Comparative Example 3 it has been tried in vain to find conditions for extruding and processing it between 150° C. and 190° C., at intervals of 5° C., but all attempts have failed.

Even independently from its non-processability, the adhesive formulation of Comparative Example 3 is already since the moment of its application from the molten state, a too hard and too crystalline adhesive for giving good adhesive bonds. So it's only for completeness of documentation that one can record the further variations of its crystalline level and of its rheological parameters with aging. About crystalline content, the unacceptably too high initial value of Crystallization Enthalpy equal to 17.3 J/g, after seven days of aging at 23° C. and 50% Relative Humidity, increases to 29.9 J/g with a percent variation of 72.8% that is anyhow (for the same reasons already described above about the previous Comparative Example) completely useless in positively influencing the strength of a possible aged adhesive bond. Similar considerations are valid also for the observed variations of its rheological parameters: e.g. the Elastic Modulus G', measured at 23° C. and 1 Hz, that from an unacceptably high value of 12.895 MPa at Time Zero further increases to as much as 19.031 MPa after seven days of aging, i.e. formally with a percent increase of 47.5%; or its Tan Delta at 23° C. and 1 Hz that from an initial very low level of 0.164 (adhesive too hard since Time Zero) decreases to 0.119 with a decrease in percentage of −27.4%.

COMPARATIVE EXAMPLE 4

The below hot-melt adhesive formulation has been prepared by mixing its constituents in the molten state at 170° C. and by following the teachings of a part of the Prior Art:

| Ingredient | % by weight on the total weight of the adhesive formulation | Nature and supplier |
|---|---|---|
| Rextac 2304 | 81.5 | Non-stereospecific Polyolefinic Copolymer supplied by Rextac (USA) |
| Vistamaxx 6202 | 5.0 | Semi-crystalline polyolefinic elastomer supplied by ExxonMobil (USA) |
| Epolene N-21 | 10.0 | Polyethylenic cristalline wax supplied by Westlake (USA) |
| AC-596 | 2.0 | Polypropylenic wax modified with maleic anhydride, supplied by Honeywell (USA) |
| Irgafos 168 | 1.0 | Antioxidant supplied by BASF (Germany) |
| Irganox 1010 | 0.5 | Antioxidant supplied by BASF (Germany) |

In the adhesive formulation of Comparative Example 4, because the molecular weight of the non-stereospecific polyolefinic copolymer Rextac 2304 is rather low (as already seen) and because, as a consequence, this adhesive has too low cohesion, the Prior Art of this Comparative Example teaches to blend Rextac 2304 with a semi-crystalline and hetero-phasic elastomer, synthesized from propylene and ethylene, Vistamaxx 6202, supplied by ExxonMobil. This elastomer contains a phase made of highly crystalline isotactic polypropylene intimately blended with a more amorphous phase of a rubbery copolymer C2-C3. This elastomer has an initial Crystallization Enthalpy that is not too high and equal to 7.8 J/g; however it has a very high molecular weight, as indicated by its melt viscosity that at 190° C. is as high as about 700,000 mPa·s. In fact its average Number Molecular Weight Mn is believed to be equal to 69,600 g/mole and its average Mass Molecular Weight Mw equal to 144,700 g/mole.

Moreover the Prior Art teaches to further increase the initial crystallinity of this adhesive formulation, so to achieve an acceptable initial cohesion, by adding 10% by weight of highly crystalline polyethylenic wax, Epolene N-21, supplied by Westlake (USA) as well as 2% by weight of AC 596, a polypropylenic wax modified with maleic anhydride. As a result, the adhesive formulation of comparative Example 4 has a high initial crystallinity, as showed by its initial Crystallization Enthalpy that is equal to 16 J/g.

Also its Solidification Rate around its Rheological setting point (that is equal to 92.9° C.) is unacceptably high and equal to as much as −21,700 Pa/° C., as well as its Decreasing Rate of Tan Delta that is as high as 1.08 (° C.)$^{-1}$.

This adhesive formulation has a melt viscosity of 3,400 mPa·s at 150° C. and of 1,400 mPa·s at 170° C.; it has a high Ring & Ball Softening Point equal to 136.1° C., and it is also hard having a Needle Penetration at 55° C. equal to 60 dmm.

When this formulation has been processed at 300 m/minute, for bonding a perforated polyethylene film, in the already described conditions, it has showed a negligible aged adhesive Peel strength equal only to 0.1 N/inch (0.039 N/cm—see Table 1).

For the too crystalline and too rapidly setting adhesive formulation of the present Comparative Example 4, are even more valid the considerations made about the two previous Comparative Examples and concerning the uselessness of observing the variations with aging of crystallinity and of rheological parameters, for adhesives that are unable to form—for whatever reason; in this case for the excessive initial crystallinity and the too fast setting rate—good initial adhesive bonds because of the missing of a good initial wetting of the substrate, of a sufficiently wide contact area between adhesive and substrate etc. Anyhow, for documentation, the adhesive formulation of Comparative Example 4, that has a too high initial Crystalline Enthalpy of 16 J/g, after seven days of aging further increases its Crystalline Enthalpy to 24.1 J/g with a variation of 50.6%. These variations with aging are even more evident—but still fully useless for improving the very poor initial adhesive strength—with the rheological parameter Elastic Modulus G', that, measured at 23° C. and 1 Hz, has at Time Zero an excessive value (adhesive too hard and not tacky) of 10.46 MPa that further increases in aging to as much as 24.833 MPa, with a formal percent variations of 137.4%. On the contrary, to once more demonstrate that this comparative formulation is an unacceptably too hard adhesive with no capability of wetting a substrate and giving good bond strength, the other rheological parameter Tan Delta, at 23° C. and 1 Hz, shows a too low value already at Time Zero, equal to 0.179, that minimally decreases with aging, passing after seven days to 0.174, i.e. with a decrease in percentage as low as −2.8%.

COMPARATIVE EXAMPLE 5

The below hot-melt adhesive formulation has been prepared by mixing its constituents in the molten state at 170° C. and by following the teachings of a part of the Prior Art:

| Ingredient | % by weight on the total weight of the adhesive formulation | Nature and supplier |
| --- | --- | --- |
| Rextac E-65 | 60.0 | Non-stereospecific Polyolefinic Copolymer supplied by Rextac (USA) |
| Vistamaxx 8880 | 35.0 | Semi-crystalline polyolefinic elastomer supplied by ExxonMobil (USA) |
| Indopol H-300 | 4.5 | Poly-iso-butylene plasticizing oil (PIB) supplied by Ineos Oligomers (Switzerland) |
| Irganox 1010 | 1.5 | Antioxidant supplied by BASF (Germany) |

The adhesive formulation of Comparative Example 5 comprises, as its main polymer constituent, a non-stereospecific polyolefinic copolymer Rextac E-65, supplied by Rextac (USA). This polymer is believed to be a copolymer of butene-1 and propylene, containing about 60% by mole of butene-1, with an average Number Molecular Weight of about 9,700 g/mole and an average Mass Molecular Weight of about 68,500 g/mole. Even if this copolymer is sold as a non-stereospecific polymer, actually its initial residual crystallinity seems unusually high for such a type of polymer; in fact its initial Crystallization Enthalpy is equal to as much as 32.9 J/g.

Similarly to what seen in the previous Comparative Example 4, some Prior Art teaches to blend also this already highly crystalline Rextac polymer with substantial quantities of a semi-crystalline Vistamaxx elastomer.

However, still for keeping an adequate initial cohesion, because the Rextac polymer used here has per se a high crystallinity, the type of Vistamaxx blended in this formulation, i.e. Vistamaxx 8880, can have a lower molecular weight and viscosity than Vistamaxx 6202, used in the previous example, even if its initial crystallinity continues to be high. In fact Vistamaxx 8880 has an average Number Molecular Weight Mn equal to about 12,900 g/mole and an average Mass Molecular Weight equal to about 27,000 g/mole; but its initial crystallinity is high as showed by its Crystallization Enthalpy at Time Zero equal to as much as 26.6 J/g. As a consequence, the adhesive formulation of Comparative Example 5 has a high initial residual crystallinity, as showed by its initial Crystallization Enthalpy that is equal to as much as 25.3 J/g.

Also its Solidification Rate and its Decreasing Rate of Tan Delta, around its Rheological setting Point (that is 54.7° C.) are high, i.e. as much as −38,500 Pa/° C. for the first parameter and 0.36 (° C.)$^{-1}$ for the second parameter.

For completeness of information, the adhesive formulation of Comparative Example 5 has a viscosity at 150° C. equal to 5,000 mPa·s; a viscosity at 170° C. equal to 2,860 mPa·s; a Ring & Ball Softening Point of 105.8° C.; a Needle Penetration at 55° C. equal to 30 dmm (i.e. this adhesive is unacceptably hard) and an Open Time of about 3 minutes.

For improving its processability, the hot-melt adhesive formulation of Comparative Example 5 comprises 4.5% by weight of a liquid oligomeric plasticizer that is a poly-iso-butylene oil (PIB), traded by Ineos Oligomers (Switzerland) with the trade mark Indopol H-300. However, in spite of the presence of this plasticizer and similarly to what seen for previous Comparative Examples, the present comparative adhesive formulation could not be regularly extruded and processed at the line speed of 300 m/minute and in the whole range of temperatures between 150° C. and 190° C.

Even besides its non-processability, also the characteristics of variations with aging of the adhesive formulation of Comparative Example 5 are unsatisfactory. In fact, for example, the extraordinarily too high initial crystallinity, as expressed by a Crystallinity Enthalpy at Time Zero equal to as much as 25.3 J/g, after aging for seven days at 23° C. and 50% Relative humidity, increases to an aged Crystallinity Enthalpy of 29.5 J/g, with a percent variation of 16.6%. The Elastic Modulus G', measured at 23° C. and 1 Hz, has at Time Zero the high (for a good adhesive) value of 18.75 MPa, well expressing the excessive hardness and inability to wet the substrate of this adhesive; said Elastic Modulus, after seven days of aging, further increases to 28.12 MPa, formally with a variation in percentage of 49.9%, but without any positive influence, for the already mentioned reasons, on the strength of possible adhesive bonds. Finally what said is true even more for Tan Delta and so for the ability of this adhesive of correctly wet the substrates; in fact Tan Delta, measured at 23° C. and 1 Hz has an unacceptably low initial value of 0.140, and after aging it decreases to 0.106 with a percent variation of −24.3%.

COMPARATIVE EXAMPLE 6

The below hot-melt adhesive formulation has been prepared by mixing its constituents in the molten state at 170° C. and by following the teachings of a part of the Prior Art:

| Ingredient | % by weight on the total weight of the adhesive formulation | Nature and supplier |
|---|---|---|
| Rextac E-65 | 60.0 | Non-stereospecific Polyolefinic Copolymer supplied by Rextac (USA) |
| Vistamaxx 8880 | 10.0 | Semi-crystalline polyolefinic elastomer supplied by ExxonMobil (USA) |
| Indopol H-1900 | 29.5 | Poly-iso-butylene plasticizing oil (PIB) supplied by Ineos Oligomers (Switzerland) |
| Irganox 1010 | 1.5 | Antioxidant supplied by BASF (Germany) |

The adhesive formulation of Comparative Example 6 is very similar to the one of Comparative Example 5. In this case, to try to attain a good processability, the Prior Art has very much increased the content of the liquid plasticizer, i.e. the poly-iso-butylene plasticizing oil (PIB) Indopol H-1900, increasing its percentage up to 29.5% by weight.

Thanks to this it has been possible to extrude and process at 300 m/minute the adhesive formulation of Comparative Example 6, differently from what seen for the analogous formulation of Comparative Example 5. However, as showed in the following Table 1, the adhesive Peel Strength in bonding the perforated plastic film has been unacceptably low being equal just to 0.3 N/inch (0.118 N/cm).

About the other characteristics, the adhesive formulation of Comparative Example 6 shows the following main parameters: Crystallization Enthalpy at Time Zero=17.2 J/g; Rheological Setting Point=44.5° C.; Solidification Rate around said point=−8,820 Pa/° C.; Decreasing Rate of Tan Delta around said point=0.18 (° C.)$^{-1}$; viscosity at 150° C.=4,700 mPa·s; viscosity at 170° C.=2,520 mPa·s; Ring & Ball Softening Point=104.4° C.; Needle Penetration at 55° C.=45 dmm; Open Time equal to about 5 minutes.

Also the variations with aging of the level of crystallinity and of the rheological parameters of the adhesive formulation of Comparative Example 6 are totally unsatisfactory; and in any case—as already illustrated for previous comparative examples—useless for positively influencing the value of the final aged adhesive Peel Strength, that anyhow remains unsatisfactorily low. For documentation, the formulation of Comparative Example 6 has a too high initial crystallinity as expressed by a Crystalline Enthalpy at Time Zero of 17.2 J/g that after seven days of aging at 23° C. and 50% Relative Humidity, slightly increases to 18 J/g, with a percent variation of 4.7%. Its very high initial Elastic Modulus G', measured at 23° C. and 1 Hz, has a value of as much as 10.58 MPa that further hardens with aging to 14.101 MPa, increasing in percent of 33.2%; equally its unacceptably low Tan Delta at Time Zero, still measured at 23° C. and 1 Hz, has the too low value of 0.172 and after aging further decreases to 0.128 with a variation in percentage of −25.5%.

COMPARATIVE EXAMPLE 7

The following hot-melt adhesive formulation has been prepared by mixing its constituents in the molten state at 170° C. but not observing all the teachings and requirements of the present invention and following the teachings of a part of the Prior Art:

| Ingredient | % by weight on the total weight of the adhesive formulation | Nature and supplier |
|---|---|---|
| Rextac 2830 | 59.9 | Non-stereospecific Polyolefinic Copolymer supplied by Rextac (USA) |
| L-Modu S400 | 19.9 | Semi-crystalline polypropylene supplied by Idemitsu Kosan (Japan) |
| Escorez 5400 | 19.9 | Hydrogenated hydrocarbon tackifier supplied by ExxonMobil (USA) |
| Irganox 1010 | 0.3 | Antioxidant supplied by BASF (Germany) |

Like in the previous Comparative Examples, also the hot-melt adhesive formulation of Comparative Example 7 tries to balance a good initial adhesiveness, given by the non-stereospecific polyolefinic copolymer Rextac 2830, with a good initial cohesion, given by the addition of about 20% by weight of a polypropylene L-Modu S400, that is said to be a bi-phasic polymer, i.e. containing both chain segments of isotactic polypropylene at very high crystallinity, that are alternated with segments of a substantially atactic polypropylene.

Therefore already per se, the polypropylene L-Modu S400 should be a "compromise" between a certain level of adhesiveness (given by the fraction of amorphous atactic molecules) and of acceptable initial cohesion (given by the zones formed by isotactic polypropylene, at very high crystallinity and hardness).

The base non-stereospecific copolymer, Rextac 2830, is a copolymer containing about 55% by mole butene-1, and 45% by mole propylene. It is believed to have an average Number Molecular Weight Mn of about 9,300 g/mole, and an average Mass Molecular Weight Mw of about 66,000 g/mole; in spite of its supposed and advertised non-stereospecificity, the actual initial residual crystallinity of Rextac 2830 is quite high as showed by its initial Crystallization Enthalpy as high as 21.5 J/g.

The bi-phasic semi-crystalline polypropylene L-Modu S400 is believed to have an average Number Molecular Weight Mn of about 26,100 g/mole and an average Mass Molecular Weight Mw of about 47,000 g/mole. It has a viscosity at 190° C. equal to 8,500 mPa·s.

Its behavior in the thermal analysis DSC is quite peculiar. When tested with the DSC test according to the three thermal cycles at time zero, as illustrated in details above, shows in the initial cooling cycle, between +180° C. and −70° C., at the cooling rate of 1° C./minute, an exothermic crystallization peak that is relatively small, with a maximum at about 46.5° C., and an apparently low initial Crystallization Enthalpy equal to 7.07 J/g.I.e. L-Modu S400 apparently behaves, from the point of view of its DSC thermal analysis, as if it had a very low level of initial crystallinity, of the order of some typical non-stereospecific polymers with a very low crystallinity like for example the above mentioned Rextac 2730.

In spite of the fact that the manufacturer does not declare the percentage of crystallinity at the thermodynamic equilibrium of this semi-crystalline polypropylene, the above illustrated behavior appears in contrast with the asserted presence, in the molecule of L-Modu S400, of a substantial fraction of zones at very high crystallinity, formed by isotactic polypropylene, as explicitly declared by the same supplier.

In fact, by completing the DSC thermal analysis of L-Modu S400 at time zero with the above described three DSC cycles, it is possible to realize that the apparently low value of the initial Crystallization Enthalpy in the cooling phase, is not due to a real absence of initial crystallinity, like in the case of non-stereospecific polymers that truly possess a very low initial crystallinity, like Rextac 2730 and Rextac 2715, but is due only to a kinetic effect. Probably thanks to its peculiar bi-phasic molecular structure, L-Modu S400 shows an initial crystallization kinetics that is particularly slow. However in these conditions the actual initial crystallinity of this polymer is in a situation of thermodynamic instability. In fact, in the following and last DSC phase in heating, from −70° C. to +180° C., this semi-crystalline polypropylene shows a totally different behavior: when the temperature increases over its Tg, this polymer shows in fact a sudden and very rapid second crystallization at Time Zero, with an exothermic crystallization peak centered around 9.9° C.

At this point, the polymer is now in its real conditions of equilibrium crystallinity at time zero. By further increasing the temperature, L-Modu S400 shows a broad endothermic peak, centered around 78.6° C., for the melting of its overall crystallinity at time zero that corresponds to a high Melting Enthalpy equal to 28.9 J/g.

Such a peculiar behavior of the initial crystallinity, misrepresented in its real initial value by a mere kinetic factor, is reflected from the constituent L-Modu S400 also in the DSC behavior at time zero of the adhesive formulation of Comparative Example 7.

In fact it shows in the cooling phase from +180° C. to −70° C., an initial Crystallization Enthalpy that is apparently quite low and equal to 3.9 J/g; however, by thermodynamic re-equilibration, it is immediately followed, in the subsequent heating phase, from −70° C. to +180° C., by further exothermic delayed crystallization peaks. In fact when the temperature increases over its Tg, the hot-melt adhesive formulation of Comparative Example 7 shows an overall endothermic melting peak that corresponds to an initial Melting Enthalpy of 10.7 J/g. Therefore this value represents the actual level of crystallinity at Time Zero of the adhesive formulation of Comparative Example 7.

It is however opportune to notice the following point: even if we should not take into account the relatively high crystallinity of the crystalline and partially isotactic polypropylene L-Modu S400 (crystallinity that appears slightly delayed in the DSC test simply due to a kinetic effect) and even if we should consider this polymer as a "pseudo-non-stereospecific" polymer, a polymer composition composed by Rextac 2830 and L-Modu S400, like the one contained in the above formulation, has not an overall unique distribution of molecular weights and with a bimodal structure.

In fact its distribution of molecular weights is definitely divided into two separate and distinct distributions owing to the excessive difference between the average molecular weights of the two polymers. In fact if one considers the difference between the average Number Molecular Weights of Rextac 2830 and L-Modu S400, Mn(A)−Mn(B), this difference is equal to as much as 16,800 g/mole; while the difference between their average Mass Molecular weights, Mw(A)−Mw(B), is even greater and equal to 19,000 g/mole.

Presumably, because the addition of a partially isotactic polypropylene like L-Modu S400, may impair the good initial adhesiveness and tackiness of the base non-stereospecific copolymer Rextac 2830, this Prior Art teaches that it is necessary to further add as much as almost 20% by weight of a hydrogenated polycyclic hydrocarbon tackifier, Escorez 5400, supplied by Exxon Mobil and having a softening point of about 103° C.

In this way however are potentially introduced—as already highlighted—various problems connected with the use of high quantities of additives at low molecular weight, like first of all malodors and possible demixing/migrations with time outside of the adhesive, besides the presence of possible residues of toxic, sensitizing or allergenic unreacted monomers, all problems that it is particularly important to avoid especially in the manufacturing of absorbent hygienic articles.

In any case, in spite of its relatively low initial Crystallinity, and of the properties connected with it, like a slow Solidification Rate, equal to 1,530 Pa/° C. and a slow Decreasing Rate of Tan Delta, equal to 0.03 (° C.)$^{-1}$, actually the adhesive formulation of Comparative Example 7 suffers from a grave drawback that make impossible for it a correct processing and application as a hot-melt adhesive in the manufacturing of absorbent hygienic articles, on industrial lines that operate at high speed, like e.g. 300 m/minute.

This fully unsatisfactory parameter of the adhesive formulation of Comparative Example 7is its Rheological Setting Point (i.e. the temperature at which the two rheological Moduli cross over room temperature) that is exceptionally low and equal to just 30.6° C.

It is evident for every person averagely expert in the use and processing of hot-melt adhesives, that, especially in the manufacturing of absorbent hygienic articles, that an adhesive with such an extraordinarily low rheological setting point, that is not only so riskily close to room temperature, but that is even largely lower than the temperature of the human body, makes—besides every other possible consideration—said adhesive practically not usable in the manufacturing of absorbent hygienic articles that are used in intimate contact with the human body. The adhesive formulation of Comparative Example 7, has a melt viscosity equalt to 9,500 mPa·s at 150° C. and to 5,130 mPa·s at 170° C.

Its Needle Penetration at 55° C. is equal to 55 dmm; it shows also a Ring & Ball Softening Point of 86.4° C. and a rather long Open Time, equal to about 13 minutes.

However, the overall characteristics of this adhesive formulation makes it globally unsatisfactory, and in any case not processable on high speed lines, operating e.g. at 300 m/minute, for the manufacturing of absorbent hygienic articles.

In fact, like for other formulations of some previous Comparative Examples, it has been attempted to extrude and process the adhesive formulation of Comparative Example 7 on a semi-industrial pilot line at 300 m/minute in the already described bonding of a perforated polyethylene film, varying the extruding temperature between 150° C. and 190° C., at steps of 5° C. But all attempts have been useless, and the adhesive formulation of Comparative Example 7 has showed to be fully non-processable in the above mentioned line conditions, that mimic a standard and real industrial line for the manufacturing of absorbing hygienic articles.

Like for previous comparative examples, the non-processability of the adhesive formulation of Comparative Example 7, obviously make useless the observed variations with aging of its crystalline level and of its rheological parameters. Anyhow for sake of documentation, the hot-melt adhesive of Comparative Example 7, that, as above mentioned has an initial crystallinity level expressed by the Crystalline Enthalpy of 10.7 J/g, after seven days of aging at 23° C. and 50% Relative Humidity, shows a Crystalline Enthalpy increased to 17.5 J/g, therefore with a percent variation of 63.6%. The variations with aging in rheological parameters are apparently even much more dramatic but of course have a pure academic value because this adhesive cannot be processed and has an excessively low Setting Temperature. Again for the sake of completeness of the present documentation, the adhesive formulation of Comparative Example 7 has an Elastic Modulus G', measured at 23° and 1 Hz that is rather low and equal to 2.226 MPa; this value, upon aging, increases very much due to the delayed crystallization of the highly crystalline segments of isotactic polypropylene contained in the crystalline constituent L-Modu S400; in fact, after seven days of aging, the value of G' has increased to the even too hard level of 12.696 MPa, with formally a percent increase of as much as 470.3%. This effect of the delayed crystallization of isotactic polypropylene is apparently less evident in the variation upon aging of the other rheological parameter Tan Delta. In fact Tan Delta, measured at 23° C. and 1 Hz, at Time Zero has the high value of 0.822, that after aging falls to 0.295, with a decrease in percent of −61.1%.

Summarizing Tables of Experimental Results

Table 1 summarizes the results of all the tests for final aged adhesive Peel strength in the test of bonding a perforated polyethylene film with a non-perforated polyethylene film, made on a pilot line operated at a line speed of 300 m/minute and at an extrusion temperature of 175° C., according to the bonding and testing conditions previously described in details:

TABLE 1

| Formulation | Aged Adhesive Peel Strength (N/inch) |
| --- | --- |
| Example 1 | 1.7 |
| Example 2 | 1.6 |
| Example 3 | 1.9 |
| Example 4 | 1.6 |
| Comparative Example 1 | Not processable |
| Comparative Example 2 | 0.2 |
| Comparative Example 3 | Not processable |
| Comparative Example 4 | 0.1 |
| Comparative Example 5 | Not processable |
| Comparative Example 6 | 0.3 |
| Comparative Example 7 | Not processable |

Table 2, Table 3 and Table 4 show the effect of aging for seven days at 23° C. and 50% relative humidity, on the hot-melt adhesive formulations of the four Examples according to the present invention, and of the seven Comparative Examples.

Table 2 shows the increments in time of the crystalline content expressed as variation of the Crystalline Enthalpy, measured in crystallization or in melting, according to what previously explained in details; while Table 3 and Table 4 show respectively the increments in time of the respective Elastic Modulus G' and the decrements in Tan Delta measured at 23° C. and at the frequency of 1 Hz.

TABLE 2

| Formulation | Crystalline Enthalpy at Time Zero (J/g) | Crystalline Enthalpy after aging (J/g) | Increment % | Notes |
| --- | --- | --- | --- | --- |
| Example 1 | 4.0 | 7.2 | 80.0% | Excellent for processability and adhesion |
| Example 2 | 4.3 | 8.8 | 104.7% | Excellent for processability and adhesion |
| Example 3 | 3.6 | 6.3 | 75.0% | Excellent for processability and adhesion |
| Example 4 | 3.7 | 6.5 | 75.7% | Excellent for processability and adhesion |
| Comparative Example 1 | 4.3 | 6.6 | 53.5% | Not processable. High viscosity |
| Comparative Example 2 | 12.2 | 16.1 | 32.0% | Unacceptably low adhesion. Too short Open Time Too fast setting rate |
| Comparative Example 3 | 17.3 | 29.9 | 72.8% | Not processable. High initial crystallinity Softening Point too high. Very high viscosity |
| Comparative Example 4 | 16.0 | 24.1 | 50.6% | Unacceptably low adhesion. High initial crystallinity. Too fast setting rate |
| Comparative Example 5 | 25.3 | 29.5 | 16.6% | Not processable Very high initial crystallinity. Too fast setting rate |
| Comparative Example 6 | 17.2 | 18.0 | 4.7% | Unacceptably low adhesion High initial crystallinity. |
| Comparative Example 7 | 10.7 | 17.5 | 63.6% | Not processable Too low Setting Temperature High viscosity |

TABLE 3

| Formulation | Elastic Modulus G' at 23° C. and 1 Hz at Time Zero (MPa) | Elastic Modulus G' at 23° C. and 1 Hz after aging (MPa) | Increment % | Notes |
| --- | --- | --- | --- | --- |
| Example 1 | 1.285 | 2.593 | +101.8 | Excellent for processability and adhesion |
| Example 2 | 1.165 | 2.289 | +96.5 | Excellent for processability and adhesion |

TABLE 3-continued

| Formulation | Elastic Modulus G' at 23° C. and 1 Hz at Time Zero (MPa) | Elastic Modulus G' at 23° C. and 1 Hz after aging (MPa) | Increment % | Notes |
|---|---|---|---|---|
| Example 3 | 1.244 | 2.492 | +100.3 | Excellent for processability and adhesion |
| Example 4 | 1.121 | 1.935 | +72.6 | Excellent for processability and adhesion |
| Comparative Example 1 | 1.294 | 1.597 | +23.4 | Not processable. High viscosity Low hardening with aging |
| Comparative Example 2 | 1.823 | 3532 | +93.7 | Unacceptably low adhesion. Too short Open Time Too fast setting rate |
| Comparative Example 3 | 12.895 | 19.031 | +47.5 | Not processable. High initial crystallinity Softening Point too high. Very high viscosity |
| Comparative Example 4 | 10.460 | 24.833 | +137.4 | Unacceptably low adhesion. High initial crystallinity. Too fast setting rate. Too hard adhesive |
| Comparative Example 5 | 18.750 | 28.120 | +49.9 | Not processable Very high initial crystallinity. Too fast setting rate. Too hard adhesive |
| Comparative Example 6 | 10.580 | 14.101 | +33.2 | Unacceptably low adhesion High initial crystallinity. Too hard adhesive |
| Comparative Example 7 | 2.226 | 12.696 | +470.3 | Not processable Too low Setting Temperature High viscosity. Too hard adhesive after aging |

TABLE 4

| Formulation | Tan Delta at 23° C. and. 1 Hz at Time Zero (MPa) | Tan Delta at 23° C. and 1 Hz after aging (MPa) | Decrement % | Notes |
|---|---|---|---|---|
| Example 1 | 0.450 | 0.240 | −46.7 | Excellent for processability and adhesion |
| Example 2 | 0.472 | 0.275 | −41.7 | Excellent for processability and adhesion |
| Example 3 | 0.457 | 0.253 | −44.6 | Excellent for processability and adhesion |
| Example 4 | 0.477 | 0.266 | −44.2 | Excellent for processability and adhesion |

TABLE 4-continued

| Formulation | Tan Delta at 23° C. and. 1 Hz at Time Zero (MPa) | Tan Delta at 23° C. and 1 Hz after aging (MPa) | Decrement % | Notes |
|---|---|---|---|---|
| Comparative Example 1 | 0.419 | 0.342 | −18.4 | Not processable. High viscosity Low hardening with aging |
| Comparative Example 2 | 0.364 | 0.320 | −12.1 | Unacceptably low adhesion. Too short Open Time Too fast setting rate |
| Comparative Example 3 | 0.164 | 0.119 | −27.4 | Not processable. High initial crystallinity Softening Point too high. Very high viscosity |
| Comparative Example 4 | 0.179 | 0.174 | −2.8 | Unacceptably low adhesion. High initial crystallinity. Too fast setting rate. Too hard adhesive |
| Comparative Example 5 | 0.140 | 0.106 | −24.3 | Not processable Very high initial crystallinity. Too fast setting rate. Too hard adhesive |
| Comparative Example 6 | 0.172 | 0.128 | −25.5 | Unacceptably low adhesion High initial crystallinity. Too hard adhesive |
| Comparative Example 7 | 0.822 | 0.295 | −64.1 | Not processable Too low Setting Temperature High viscosity. Too hard adhesive after aging |

Finally Table 5 shows, for the adhesive formulations of the four Examples according to the invention, the values of their aged Elastic Modulus G', measured at 37° C. and at the frequency of 0.01 Hz. As previously illustrated these sufficiently high values of the aged G', at body temperature and at this lower frequency, well explain the excellent behavior of the present adhesives, applied inside a hygienic absorbent article, also during the use of said article on the body of the wearer.

TABLE 5

| Formulation | Aged Elastic Modulus G' at 37° C. and 0.01 Hz (Pa) |
|---|---|
| Example 1 | 443,500 |
| Example 2 | 347,800 |
| Example 3 | 300,800 |
| Example 4 | 293,500 |

What is claimed is:

1. A hot-melt adhesive formulation, characterised in that it comprises a polymer composition formed by two non-stereospecific polyolefins, said polymer composition having a melt flow rate (MFR) ranging between 10 dg/minute and 6,000 dg/minute, measured at 190° C. and under a weight of 2.16 kg, and comprising:

A) a first non stereospecific polymer formed by a homopolymer of an olefin selected from ethylene, propylene, butene-1 or hexene, or by a copolymer among the same olefins, said polymer A) being characterised by a crystallisation enthalpy from the melt at time zero not greater than 15 J/g and by an average number molecular weight Mn(A) ranging from 3,000 g/mole to 30,000 g/mole;

B) a second non stereospecific polymer formed by a homopolymer of an olefin selected from ethylene, propylene, butene-1 or hexene, or by a copolymer among the same olefins, said polymer B) being characterised by a crystallisation enthalpy from the melt at time zero not greater than 15 J/g and by an average number molecular weight Mn(B) ranging from 3,000 g/mole to 30,000 g/mole;

and where said polymer composition has a ratio by weight between the first polymeric constituent A) and the second polymeric constituent B) ranging from 1:20 to 20:1, said polymeric constituents A) and B) being selected in such a way that the difference between the average number molecular weights of A) and B), Mn(A)−Mn(B), is not greater than 3,000 g/mole said hot-melt adhesive formulation being further characterised by the fact that:

it shows a crystallisation enthalpy from the melt at time zero not greater than 12 J/g, measured by differential scanning calorimetry (DSC) at the cooling rate of 1° C./minute;

it shows a solidification rate around its rheological setting point not greater than 3,000 Pa/° C.;

it shows a decreasing rate of its rheological parameter tan delta around its own rheological setting point, that is not greater than 0.1 (° C.)$^{-1}$, and when applied between two substrates, of which at least one is a fibrous substrate or a porous plastic film or a perforated plastic film, at a basis weight comprised between 0.5 g/m$^2$ and 50 g/m$^2$, it gives to the bonded structure an adhesive peel strength, measured after seven days of aging at 23° C. and 50% relative humidity, that is greater than 0.25 N per 50 mm of width.

2. The hot-melt adhesive formulation according to claim 1), wherein the two polymeric constituents of the polymer composition, A) and B), are selected in such a way that their average mass molecular weights Mw are ranging from 15,000 g/mole to 200,000 g/mole, and the difference between said average mass molecular weights, Mw(A)–Mw(B), is not greater than 10,000 g/mole.

3. The hot-melt adhesive formulation according to claim 1), wherein the polymer composition formed by the two non-stereospecific polymers A) and B), constitutes from 50% by weight to 100% by weight of said hot-melt adhesive formulation.

4. The hot-melt adhesive formulation according to claim 1) further comprising a polymeric viscosity modifier, that is non-solid at room temperature and that has an initial crystallisation enthalpy not greater than 2 J/g in the differential scanning calorimetry (DSC) measurement of crystallisation enthalpy and at the cooling rate of 1° C./minute.

5. The hot-melt adhesive formulation according to claim 4), wherein the polymeric viscosity modifier that is non-solid at room temperature, has a viscosity that at 50° C. is not lower than 15,000 mPa·s and at 190° C. is not lower than 200 mPa·s.

6. The hot-melt adhesive formulation according to claim 4), wherein the viscosity modifier that is non-solid at room temperature is a metallocenic non-stereospecific polymer of propylene or a metallocenic non-stereospecific copolymer of propylene-ethylene.

7. The hot-melt adhesive formulation according to claim 4), wherein the viscosity modifier that is non-solid at room temperature, constitutes from zero to 10% by weight of said hot-melt adhesive formulation.

8. The hot-melt adhesive formulation according to claim 1), that comprises from zero to 5% by weight of a tackifier or of a blend of tackifiers having a ring & ball softening point ranging from 5° C. to 160° C.

9. The hot-melt adhesive formulation according to claim 8), wherein the tackifier or the blend of tackifiers is selected from the group consisting of aliphatic hydrocarbon tackifiers, partially hydrogenated aliphatic hydrocarbon tackifier derivatives, fully hydrogenated aliphatic hydrocarbon tackifier derivatives, aromatic hydrocarbon tackifiers, partially hydrogenated aromatic hydrocarbon tackifier derivatives, fully hydrogenated aromatic hydrocarbon tackifier derivatives, tackifiers formed from blends of aliphatic and aromatic hydrocarbon monomers, terpene tackifiers, partially hydrogenated terpene tackifier derivatives, fully hydrogenated terpene tackifier derivatives, rosins, rosin esters, partially hydrogenated rosin derivatives, and fully hydrogenated rosin derivatives.

10. The hot-melt adhesive formulation according to claim 8), wherein the tackifier or the blend of tackifiers have a volatile organic compound (VOC) value not higher than 1,000 ppm as determined according to the standard test method VDA 278.

11. The hot-melt adhesive formulation according to claim 1), that comprises from zero to 8% by weight, of the total adhesive formulation, of a liquid plasticiser or of a blend of liquid plasticisers, having a viscosity not greater than 10,000 mPa·s at 50° C. and selected from the group consisting of paraffinic mineral oils, naphthenic mineral oils, vegetable oils, liquid poly-iso-butylene oils (PIB), liquid esters, phthalates, benzoates, sebacates, and combinations thereof.

12. The hot-melt adhesive formulation according to claim 1), that comprises from zero to 3% by weight, of a wax or of a blend of waxes wherein said wax or blend of waxes has a Brookfield viscosity at 190° C. not greater than 300 mPa·s.

13. The hot-melt adhesive formulation according to claim 12), wherein the wax or the blend of waxes is constituted by polyolefin waxes.

14. The hot-melt adhesive formulation according to claim 13), wherein the polyolefin waxes are modified with maleic anhydride.

15. The hot-melt adhesive formulation according to claim 1), that comprises a further non-stereospecific polyolefinic copolymer, derived from mono-olefins from C2 to C6, that has an initial crystallisation enthalpy not greater than 15 J/g.

16. The hot-melt adhesive formulation according to claim 15), wherein the further non-stereospecific polyolefinic copolymer constitutes from zero to 15% by weight of the total final adhesive formulation.

17. The hot-melt adhesive formulation according to claim 1), further comprising polymeric and oligomeric constituents, except for the non-stereospecific polymers A) and B) forming the polymer composition of claim 1), exclusively derived from mono-olefins from C2 to C6 and their blend, and that is substantially free from other polymeric and oligomeric compounds, synthetic or natural, that originate from monomers that are different from the mono-olefins from C2 to C6.

18. The hot-melt adhesive formulation according to claim 1), that has a rheological setting point ranging from 40° C. to 100° C.

19. The hot-melt adhesive formulation according to claim 1), that has a Brookfield viscosity at 170° C. not greater than 6,000 mPa·s.

20. The hot-melt adhesive formulation according to claim 1), that has a Brookfield viscosity at 150° C. not greater than 10,000 mPa·s.

21. The hot-melt adhesive formulation according to claim 1), that has a shear viscosity at 160° C. and at the shear rate of 100,000 (s)$^{-1}$ that is not higher than 650 mPa·s.

22. The hot-melt adhesive formulation according to claim 1), that has a ring & ball softening point not higher than 125° C.

23. The hot-melt adhesive formulation according to claim 1), that has a needle penetration, measured at 55° C., that is not smaller than 40 dmm.

24. The hot-melt adhesive formulation according to claim 1), that has an open time ranging from 1.5 minutes and 600 minutes.

25. The hot-melt adhesive formulation according to claim 1), that after seven days of aging at 23° C. and 50% relative humidity, shows a crystallisation enthalpy, measured in a differential scanning calorimetry (DSC) melting cycle at the heating rate of 1° C./minute, that compared with the crystallization enthalpy at time zero is at least 50% higher.

26. The hot-melt adhesive formulation according to claim 1), that after seven days of aging at 23° C. and 50% relative humidity, shows an elastic modulus G', measured at 23° C. and 1 Hz, that compared with the elastic modulus G' at time zero and in the same conditions of test, is at least 50% higher.

27. The hot-melt adhesive formulation according to claim 1), that after seven days of aging at 23° C. and 50% relative humidity, shows an elastic modulus G', measured at 23° C. and 1 Hz, that is not lower than 1.3 MPa.

28. The hot-melt adhesive formulation according to claim 1), that after seven days of aging at 23° C. and 50% relative humidity, shows a tan delta, measured at 23° C. and 1 Hz, that compared with the tan delta at time zero and in the same conditions of test, is at least 30% lower.

29. The hot-melt adhesive formulation according to claim 1), that after seven days of aging at 23° C. and 50% relative humidity, shows a tan delta, measured at 23° C. and 1 Hz, that is not higher than 0.4.

30. The hot-melt adhesive formulation according to claim 1), that after seven days of aging at 23° C. and 50% relative humidity, shows an elastic nodulus G', measured at 37° C. and 0.01 Hz, that is not lower than 30,000 Pa.

31. The hot-melt adhesive formulation according to claim 1), that comprises from 0.01% by weight and 10% by weight of at least one stabiliser selected from the group consisting of antioxidants, UV-stabilisers, photo-stabilisers, and combinations thereof.

32. The hot-melt adhesive formulation according to claim 1), that comprises from zero to 10% by weight of additional constituents selected from the group consisting of mineral fillers, pigments, dyes, perfumes, surfactants, and antistatic agents.

33. A bonded structure comprising:
   a.i. a first substrate;
   a.ii. a second substrate;
   a.iii. a hot-melt adhesive formulation according to claim 1), that bonds the first and the second substrate, and that, if applied at a basis weight ranging from 0.5 g/m$^2$ to 50 g/m$^2$, gives to the bonded structure an adhesive peel strength, measured after seven days of aging at 23° C. and 50% relative humidity, not lower than 0.25 N per 50 mm of width.

34. The bonded structure according to claim 33), in which at least one substrate is a porous fibrous substrate or a porous film or a perforated film.

35. The bonded structure according to claim 34), that is manufactured with a line speed not slower than 250 m/minute and with an adhesive basis weight ranging from 1.5 g/m$^2$ and 20 g/m$^2$, and in which the adhesive peel strength, measured after seven days of aging at 23° C. and 50% relative humidity, is not lower than 0.5 N/inch.

36. A hygienic absorbent article, comprising the hot-melt adhesive formulation according to claim 1).

37. A hygienic absorbent article, comprising a bonded structure according to claim 33).

38. The article according to claim 36), wherein said article is a baby-diaper or a training pant diaper or a diaper for incontinent adults or a feminine catamenial pad.

39. The absorbent hygienic article according to claim 36, wherein the hot-melt adhesive formulation is used for at least one of the following uses: i) general construction adhesive of the whole article; ii) for bonding elastic components; iii) for strengthening and ensuring, even in use, the integrity of an absorbent core of the absorbent hygienic article; iv) for the bonding of perforated films both with a bidimensional or tridimensional structure.

40. An article comprising the hot-melt adhesive formulation according to claim 1), wherein said article is an absorbent surgical mattress or sheet or a surgery laminate for medical use or a wound-dressing product.

41. An article comprising the hot-melt adhesive formulation according to claim 1), wherein said article is a mattress or a component thereof.

* * * * *

UNITED STATES PATENT AND TRADEMARK OFFICE
CERTIFICATE OF CORRECTION

| | | |
|---|---|---|
| PATENT NO. | : 11,306,227 B2 | Page 1 of 1 |
| APPLICATION NO. | : 17/057314 | |
| DATED | : April 19, 2022 | |
| INVENTOR(S) | : Italo Corzani | |

It is certified that error appears in the above-identified patent and that said Letters Patent is hereby corrected as shown below:

On the Title Page

Item (71)
Applicant: "SAVARE' I.C. S.p.A.," should read -- SAVARE' I.C. S.r.l., --

Item (73)
Assignee: "SAVARE' I.C. S.p.A.," should read -- SAVARE' I.C. S.r.l., --

Signed and Sealed this
Thirteenth Day of September, 2022

Katherine Kelly Vidal
*Director of the United States Patent and Trademark Office*